(12) United States Patent
Bianchi et al.

(10) Patent No.: US 10,285,876 B2
(45) Date of Patent: May 14, 2019

(54) ABSORBENT ARTICLE WITH CORE-TO-BACKSHEET GLUE PATTERN COMPRISING TWO GLUES

(71) Applicant: The Procter & Gamble Company, Cincinnati, OH (US)

(72) Inventors: Ernesto Gabriel Bianchi, Oberursel (DE); Jose Mauricio Berrizbeitia, Deerfield Township, OH (US); Thorsten Rinnert, Fernwald (DE); Eric Robert Schurdak, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 678 days.

(21) Appl. No.: 14/887,358

(22) Filed: Oct. 20, 2015

(65) Prior Publication Data
US 2016/0113825 A1    Apr. 28, 2016

Related U.S. Application Data

(60) Provisional application No. 62/068,174, filed on Oct. 24, 2014.

(51) Int. Cl.
*A61F 13/49* (2006.01)
*A61F 13/539* (2006.01)
(Continued)

(52) U.S. Cl.
CPC ...... *A61F 13/539* (2013.01); *A61F 13/15699* (2013.01); *A61F 13/49* (2013.01);
(Continued)

(58) Field of Classification Search
CPC .......... A61F 13/49001; A61F 13/51104; A61F 13/51108; A61F 13/51484; A61F 13/515;
(Continued)

(56) References Cited

U.S. PATENT DOCUMENTS 3,848,594 A   11/1974   Buell
3,860,003 A   1/1975    Buell
(Continued)

FOREIGN PATENT DOCUMENTS

EP   149880     7/1985
EP   1065047    1/2001
(Continued)

OTHER PUBLICATIONS

International Search Report, PCT/US2015/056655, dated Jan. 22, 2016, 11 pages.

*Primary Examiner* — Catherine L Anderson
(74) *Attorney, Agent, or Firm* — Wednesday G. Shipp; Andrew J. Hagerty

(57) ABSTRACT

An absorbent article comprises a topsheet on the wearer-facing side, a backsheet on the garment-facing side, and an absorbent core positioned between the topsheet and the backsheet. The absorbent core comprises an absorbent material comprising a superabsorbent polymer, a core wrap enclosing the absorbent material, and a first channel disposed on one side of the longitudinal axis and a second channel disposed on the other side of the longitudinal axis.

17 Claims, 10 Drawing Sheets

(51) Int. Cl.
*A61F 13/514* (2006.01)
*A61F 13/15* (2006.01)
*A61F 13/53* (2006.01)

(52) U.S. Cl.
CPC .................. *A61F 13/514* (2013.01); *A61F 2013/530481* (2013.01); *A61F 2013/53908* (2013.01); *A61F 2013/53925* (2013.01)

(58) Field of Classification Search
CPC .... A61F 13/533; A61F 13/536; A61F 13/539; A61F 2013/15569; A61F 2013/5315; A61F 2013/53908; A61F 2013/53916; A61F 2013/53925
See application file for complete search history.

(56) References Cited

U.S. PATENT DOCUMENTS

| | | | |
|---|---|---|---|
| 3,913,580 A * | 10/1975 | Ginocchio | A61F 13/515 156/290 |
| 3,929,135 A | 12/1975 | Thompson | |
| 4,324,246 A | 4/1982 | Mullane et al. | |
| 4,342,314 A | 8/1982 | Radel et al. | |
| 4,463,045 A | 7/1984 | Ahr et al. | |
| 4,515,595 A | 5/1985 | Kievet et al. | |
| 4,609,518 A | 9/1986 | Curro et al. | |
| 4,629,643 A | 12/1986 | Curro et al. | |
| 4,662,875 A | 5/1987 | Hirotsu et al. | |
| 4,681,793 A | 7/1987 | Linman et al. | |
| 4,695,278 A | 9/1987 | Lawson | |
| 4,699,622 A | 10/1987 | Toussant et al. | |
| 4,710,189 A | 12/1987 | Lash | |
| 4,795,454 A | 1/1989 | Dragoo | |
| 4,808,178 A | 2/1989 | Aziz | |
| 4,846,815 A | 7/1989 | Scripps | |
| 4,894,060 A | 1/1990 | Nestegard | |
| 4,909,803 A | 3/1990 | Aziz | |
| 4,946,527 A | 8/1990 | Battrell | |
| 4,963,140 A | 10/1990 | Robertson et al. | |
| 5,006,394 A | 4/1991 | Baird | |
| 5,151,092 A | 9/1992 | Buell et al. | |
| 5,221,274 A | 6/1993 | Buell et al. | |
| 5,242,436 A | 9/1993 | Weil et al. | |
| 5,499,978 A | 3/1996 | Buell et al. | |
| 5,507,736 A | 4/1996 | Clear et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,607,760 A | 3/1997 | Roe | |
| 5,609,587 A | 3/1997 | Roe | |
| 5,643,588 A | 7/1997 | Roe et al. | |
| 5,700,254 A | 12/1997 | McDowall et al. | |
| 5,865,823 A | 2/1999 | Curro | |
| 5,938,648 A | 8/1999 | Lavon et al. | |
| 5,968,025 A | 10/1999 | Roe et al. | |
| 6,004,306 A | 12/1999 | Robles et al. | |
| 6,432,098 B1 | 8/2002 | Kline et al. | |
| 6,632,504 B1 | 10/2003 | Gillespie et al. | |
| 6,645,569 B2 | 11/2003 | Cramer et al. | |
| 6,716,441 B1 | 4/2004 | Roe et al. | |
| 6,790,798 B1 | 9/2004 | Suzuki et al. | |
| 6,863,933 B2 | 3/2005 | Cramer et al. | |
| 6,881,205 B2 | 4/2005 | Zehner et al. | |
| 6,946,585 B2 | 9/2005 | London Brown | |
| 6,965,058 B1 | 11/2005 | Raidel et al. | |
| 7,112,621 B2 | 9/2006 | Rohrbaugh et al. | |
| 7,160,281 B2 * | 1/2007 | LeMinh | A61F 13/539 604/385.01 |
| 7,744,576 B2 | 6/2010 | Busam et al. | |
| 7,786,341 B2 | 8/2010 | Schneider et al. | |
| 9,789,009 B2 * | 10/2017 | Joseph | A61F 13/42 |
| 2003/0105190 A1 | 6/2003 | Diehl et al. | |
| 2003/0148684 A1 | 8/2003 | Cramer et al. | |
| 2003/0158531 A1 | 8/2003 | Chmielewski | |
| 2005/0008839 A1 | 1/2005 | Cramer et al. | |
| 2006/0024433 A1 | 2/2006 | Blessing et al. | |
| 2008/0312617 A1 | 12/2008 | Hundorf et al. | |
| 2008/0312622 A1 | 12/2008 | Hundorf et al. | |
| 2010/0051166 A1 | 3/2010 | Hundorf et al. | |
| 2011/0250413 A1 | 10/2011 | Lu et al. | |
| 2011/0268932 A1 | 11/2011 | Catalan et al. | |
| 2011/0274834 A1 | 11/2011 | Brown et al. | |
| 2011/0319848 A1 | 12/2011 | McKiernan et al. | |
| 2012/0312491 A1 | 12/2012 | Jackels et al. | |
| 2012/0316523 A1 | 12/2012 | Hippe et al. | |
| 2014/0027066 A1 | 1/2014 | Jackels et al. | |
| 2014/0142531 A1 | 5/2014 | Sasayama et al. | |
| 2014/0163504 A1 | 6/2014 | Bianchi et al. | |

FOREIGN PATENT DOCUMENTS

| | | |
|---|---|---|
| EP | 2740454 | 6/2014 |
| GB | 2146887 | 5/1985 |
| JP | 2001-190594 | 7/2001 |
| JP | 2003-265521 | 9/2003 |
| JP | 2005-103178 | 4/2005 |
| JP | 2006-110025 | 4/2006 |
| JP | 2011-19730 | 2/2011 |
| JP | 5075703 B | 11/2012 |
| JP | 2013-255560 | 12/2013 |
| WO | WO95/10996 | 4/1995 |
| WO | WO95/11652 | 5/1995 |
| WO | WO95/16746 | 6/1995 |
| WO | WO95/24173 | 9/1995 |
| WO | WO2000/59430 | 10/2000 |
| WO | WO02/067809 | 9/2002 |
| WO | WO 03/037211 | 5/2003 |
| WO | WO2008/155699 | 12/2008 |
| WO | WO2011/163582 | 12/2011 |
| WO | WO2012/052172 | 4/2012 |
| WO | WO2012/170341 A1 | 12/2012 |
| WO | WO2012/170778 | 12/2012 |
| WO | WO2012/170779 | 12/2012 |
| WO | WO2012/170781 | 12/2012 |
| WO | WO2012/170808 | 12/2012 |
| WO | WO2013/069398 | 5/2013 |
| WO | WO2014/093310 | 6/2014 |
| WO | WO2014/093311 A1 | 6/2014 |

* cited by examiner

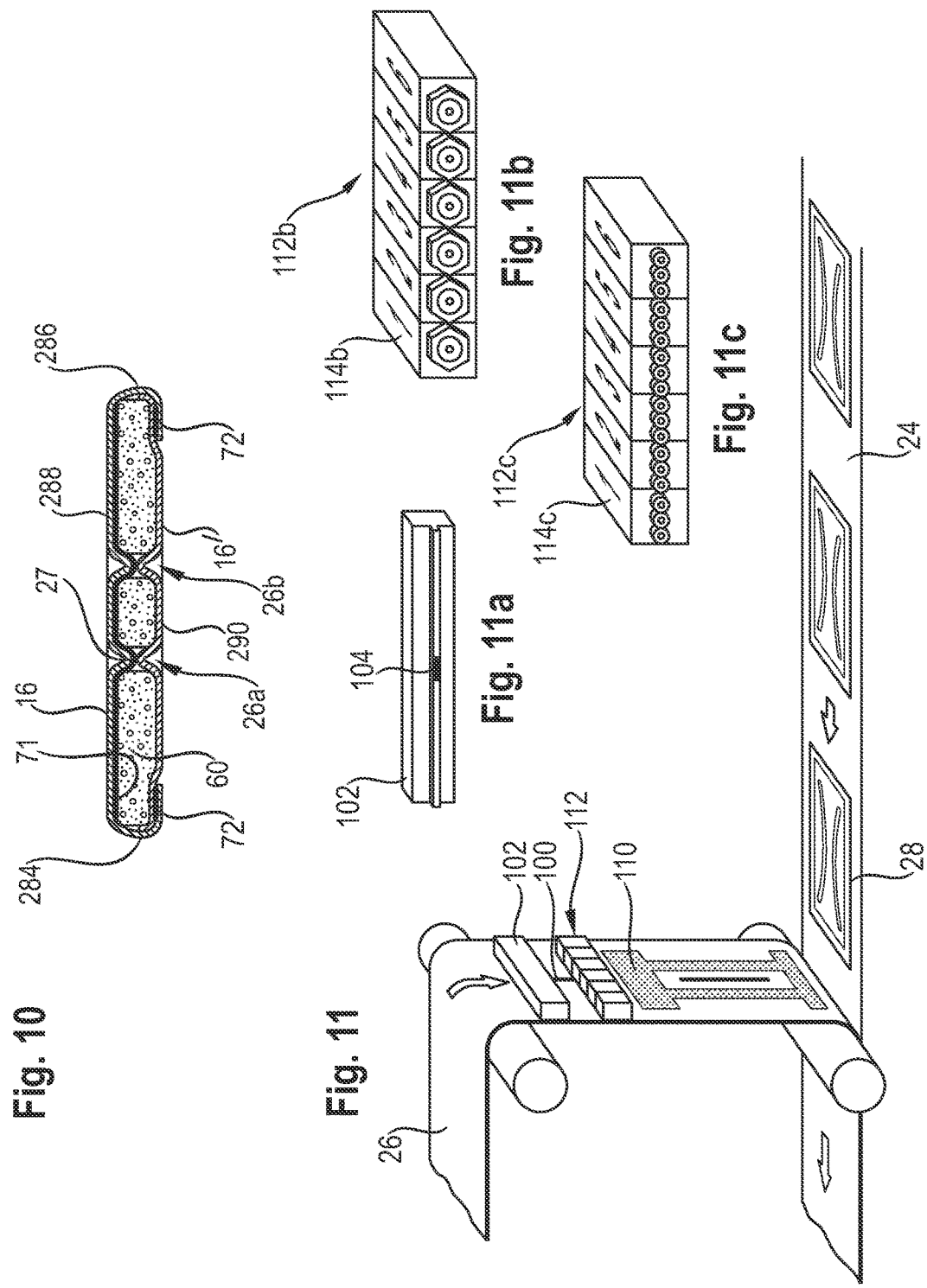

ously be used to cover large areas of the core-to-backsheet interface as it typically requires less glue material per unit of surface. The second glue application area may thus be larger than the first glue application area, in particular the second
ABSORBENT ARTICLE WITH CORE-TO-BACKSHEET GLUE PATTERN COMPRISING TWO GLUES

FIELD OF THE INVENTION

The invention relates to personal hygiene absorbent articles of the type worn in the crotch region of an individual to absorb body exudates. The absorbent articles may in particular be baby and toddler diapers (including training pants), feminine sanitary pads and/or adult incontinence articles. The present invention relates more particularly the core-to-backsheet glue pattern of these articles.

BACKGROUND OF THE INVENTION

Absorbent articles for personal hygiene of the type indicated above are designed to absorb and contain body exudates, in particular large quantity of urine. These absorbent articles comprise several layers providing different functions, for example a wearer-facing topsheet, a garment-facing backsheet and in-between an absorbent core, among other layers. The function of the absorbent core is typically to absorb and retain the exudates for a prolonged amount of time, minimize re-wet to keep the wearer dry and avoid soiling of clothes or bed sheets.

The majority of currently marketed absorbent articles comprise as absorbent material a blend of comminuted wood pulp with superabsorbent polymers (SAP) in particulate form, also called absorbent gelling materials (AGM), see for example U.S. Pat. No. 5,151,092 (Buell). Cores having an absorbent material consisting essentially of SAP (so called "airfelt-free" cores) have also been proposed, see for example WO95/11652 (Tanzer), U.S. Pat. No. 6,790,798 (Suzuki), WO2008/155699 (Hundorf), or WO2012/052172 (Van Malderen). Absorbent cores with slits or grooves have also been proposed, typically to increase the fluid acquisition properties of the core or to act as a folding guide. WO2012/170778 (Rosati et al., see also WO2012/170779, WO2012/170781 and WO2012/170808) discloses absorbent structures that comprise superabsorbent polymers, optionally a cellulosic material, and at least a pair of substantially longitudinally extending channels.

The various components of an article are typically attached to another so that they stay in place before and during usage. Typical attachment means are gluing, heat and/or pressure bonding, ultrasonic bonding. The attachment means will be chosen by the manufacturer to balance costs of the equipments, cost of the glue material and performance required. Absorbent cores are typically attached to the backsheet by gluing, in particular by spraying the whole of the backsheet with a discontinuous glue layer before attaching both components together.

Alternative core-to-backsheet gluing patterns have been proposed. WO2012/170341A1 (Hippe) discloses a diaper having a reduced core-to-backsheet gluing pattern. In Hippe, the absorbent core is attached to the backsheet only in certain, limited areas. As a consequence, the formation of buckles and wrinkles in the backsheet, as well as the see-through of urine stains from the absorbent core through the backsheet can be reduced.

The present invention is directed to an improved core-to-backsheet gluing pattern, as will be further disclosed in the following specification.

SUMMARY OF THE INVENTION

The present invention is directed to absorbent articles comprising a topsheet on the wearer-facing side, a backsheet on the garment-facing side and an absorbent core between the topsheet and the backsheet. The absorbent core comprises an absorbent material comprising a superabsorbent polymer, in particular superabsorbent particles, a core wrap enclosing the absorbent material, and a first channel disposed on one side of the longitudinal axis and a second channel disposed on the other side of the longitudinal axis.

In short, the inventors have found that it is beneficial that such absorbent cores comprising channels should be attached to the backsheet by a first glue and a second glue, each glue having a glue application area and a glue application pattern. The first glue area is at least partially present between the channels whereas the second glue has a second glue application area at least partially outside the area between the channels. The first channel and the second channel are at least partially not attached by the first glue and second glue, or otherwise, to the backsheet. The first glue has a different application pattern than the second glue. Advantageously, the absorbent core and the backsheet may only be attached by first glue and the second glue.

The inventors have surprisingly found that during the article making process, shearing forces on the backsheet or the core can concentrate along the glue edge of the second glue and rupture the backsheet substrate. The inventors have found that in presence of the first glue, the forces over the backsheet substrate are better distributed, improving not only the anchoring of the core but also preventing failures or fatigue on the backsheet during the making or wear of the absorbent article.

The inventors have also found that it can be beneficial to have different glue properties between the first and the second glue.

Further, advantageous but non-limiting features of the inventions are now briefly indicated in the rest of this summary. The glue pattern of the invention may be particularly useful for absorbent articles comprising relatively high amount of SAP. The channels may be in particular areas substantially free of absorbent material and which are surrounded by absorbent material. The top layer of the core wrap can be bonded to the bottom layer of the core through the channel areas. The first channel and the second channel may be longitudinally extending and have a length as projected on the longitudinal axis which is at least 25% of the length of the absorbent core.

The first glue, which is at least partially applied between the channels, advantageously has a first application pattern which is continuous. By "continuous" it is meant the glue forms a uniform layer or coating that covers substantially the whole surface of the area on which it is applied. Continuous pattern can be typically obtained by direct application of the glue on the substrate, such as by slot coating or printing of the glue. "Discontinuous" refers on the other hand to a glue pattern which does not form a continuous layer on the application area. A discontinuous pattern may for example comprise glue filaments, fibers or the like creating a more or less regular glue web with relatively large areas which are not covered by the glue between the glue filaments or fibers. Discontinuous areas are typically obtained by non-contact application method such as spraying of the glue.

The second glue application pattern may be advantageously discontinuous. For example it may comprise one and typically a plurality of large swirls, mini swirls or random patterns. The second glue pattern may advantageously be used to cover large areas of the core-to-backsheet interface as it typically requires less glue material per unit of surface. The second glue application area may thus be larger than the first glue application area, in particular the second glue area may be at least 3 times larger, or at least 5 times larger, than the first glue area.

The second glue application area may, at least portionwise, extend substantially along the full length of the absorbent core. In particular there may be a first longitudinally extending portion on one side of the longitudinal axis and a second longitudinally extending portion on the other side of the longitudinal axis. This provides for a secure attachment of the absorbent core along its full length. The second glue application area may further more extend at least portionwise along the full length of the backsheet, thus beyond the front and back edges of the core. This may be desirable for providing further attachment of the backsheet with other components of the article in particular the topsheet. The second glue application area may be also relatively large in the region of the front edge and the back edge of the core to provide for a stronger core-backsheet attachment in these areas, in particular to attach securely the corners of the core to the backsheet.

The present invention is also directed to a process for making an absorbent article according to the invention. In particular, such process comprises the following steps for attaching the absorbent core to the backsheet:

applying a first glue on the backsheet or the absorbent core on the first glue application area according to the first pattern, which may in particular be continuous;

applying a second glue on the backsheet or the absorbent core on the second glue application area according to the second pattern, which may in particular be discontinuous; and then bringing the core wrap and the absorbent core in contact so that they are attached by the first glue and second glue.

As indicated previously, the first glue may be applied by a contact applicator, such as a slot-coater, and the second glue may be applied by a non-contact applicator, typically a glue spray nozzle providing at least one and typically a plurality of large swirls, mini swirls or random glue patterns. The second glue may be in particular applied by a plurality of nozzles disposed in parallel, wherein for each article, at least some of the nozzles are turned on and off to provide a second glue application pattern comprising longitudinally extending second glue portion of different lengths (intermittent applications of the glue). This can allow reducing the consumption of the second glue by applying the second glue only in the desired areas, in particular wherein the second glue application area generally defines a roman II numeral shape.

BRIEF DESCRIPTION OF THE DRAWINGS

FIG. 10 is a transversal cross-section of the core of FIG. 10;

FIG. 11 is a schematic sketch of a process for applying the core to backsheet glue pattern.

FIG. 11a,b,c schematically illustrate three different applicators that may be used to apply a glue;

DETAILED DESCRIPTION OF THE INVENTION

Introduction

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular" and the likes also qualify features which are not intended to limit the scope of the claims unless specifically indicated to do so.

Unless indicated otherwise, the description and claims refer to the absorbent core and article before use (i.e. dry, and not loaded with a fluid) and conditioned at least 24 hours at 21° C.+/−2° C. and 50+/−20% Relative Humidity (RH).

The invention will now be further illustrated with reference to the embodiments as described in the Figures. For ease of discussion, the absorbent article and its components will be discussed with reference to the numerals referred to in these Figures. However it should be understood that these exemplary embodiments and the numerals are not intended to limit the scope of the claims, unless specifically indicated. Dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Figure 1:
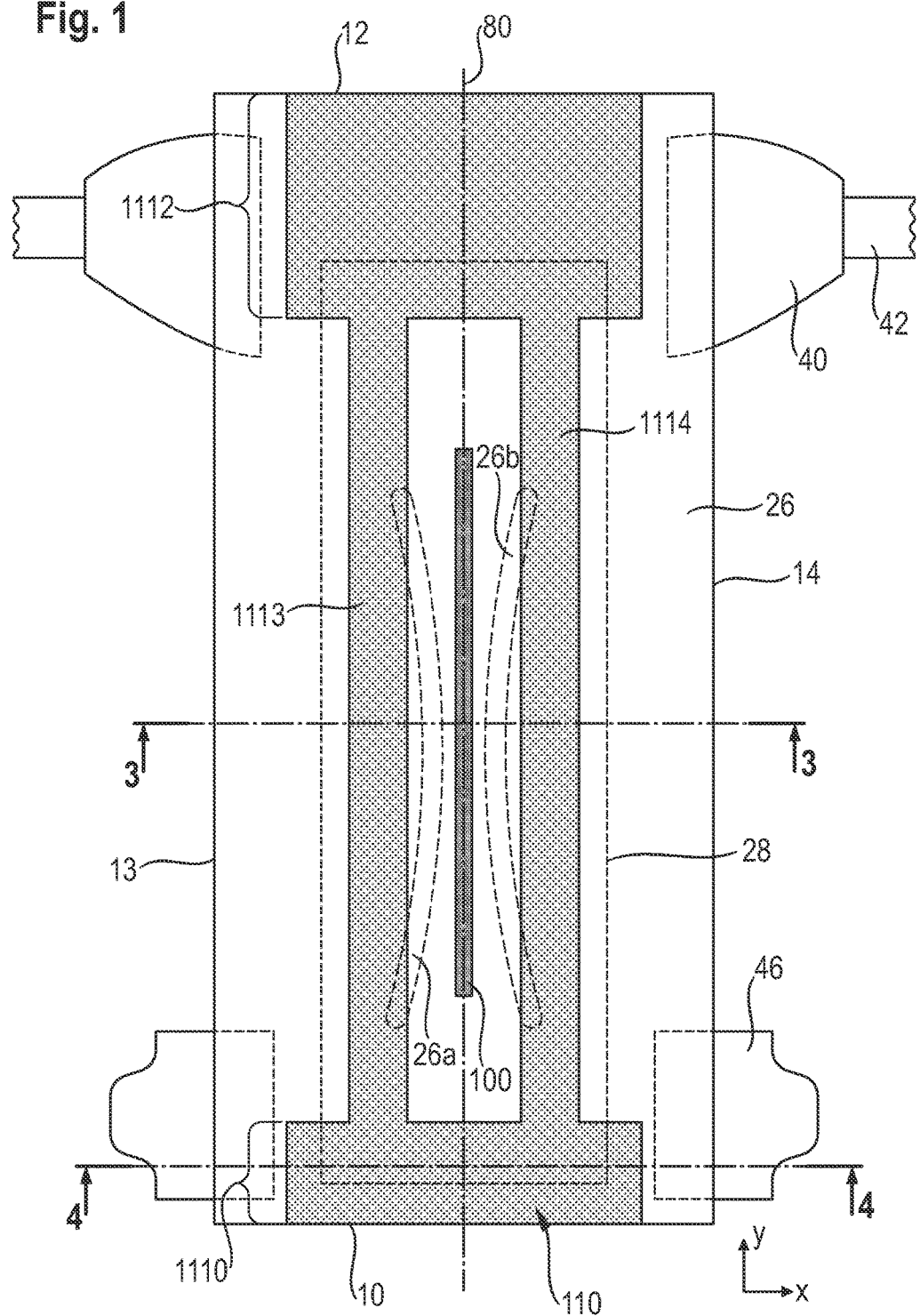
FIG. 1 shows a backsheet with a glue pattern according to the invention, with the outline of the absorbent core and its channels shown in dotted lines, the rest of the article being omitted for readability.

General Description of FIG. 1

Figure 2:
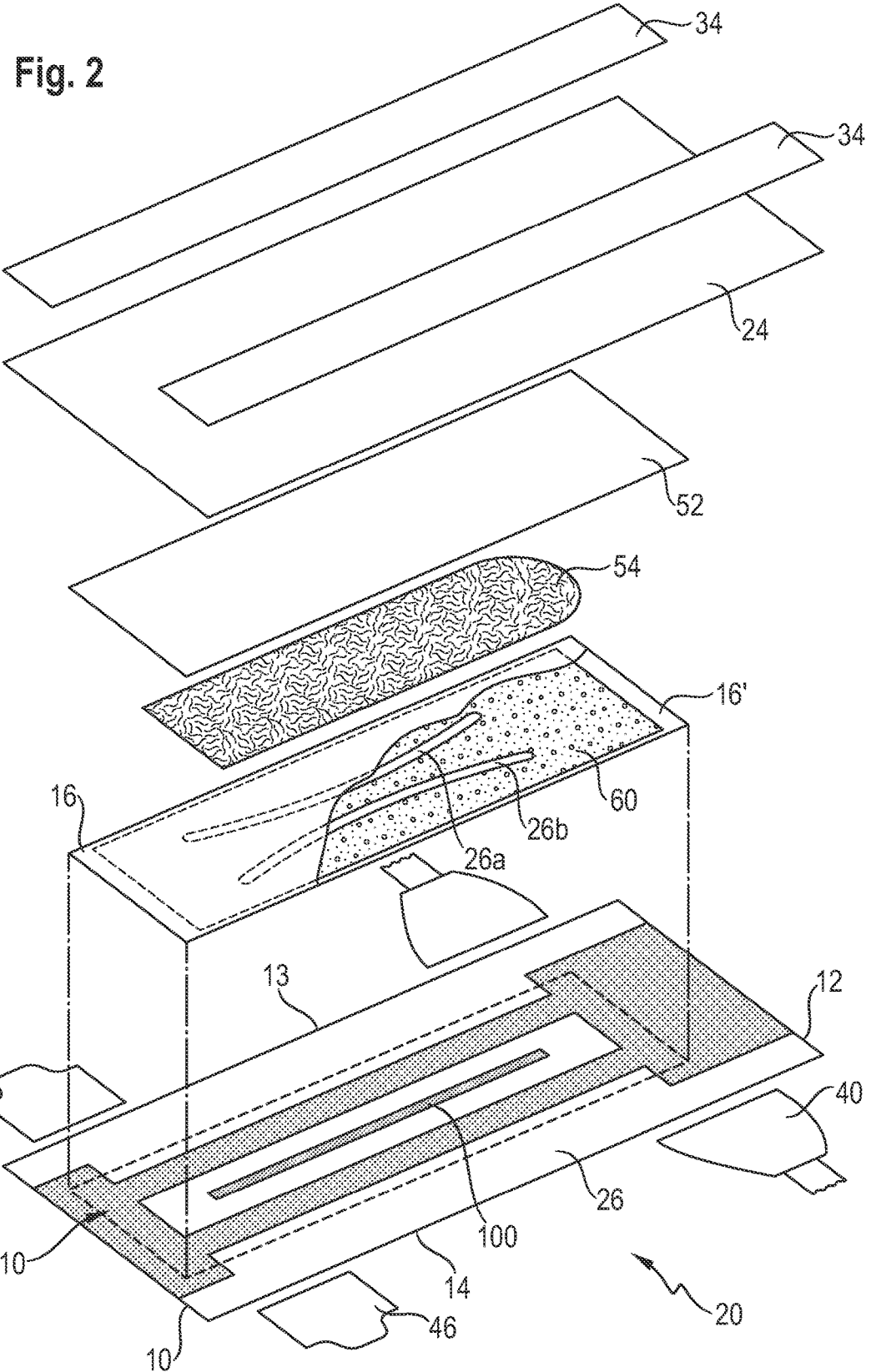
FIG. 2 shows a schematic exploded view of some of the main components of an absorbent article, including the backsheet of FIG. 1.

FIG. 1 shows an exemplary core-to-backsheet gluing pattern according to the invention. For readability, the backsheet 26 is represented in continuous line and the contour of the absorbent core 28 and of the channels 26a, 26b in broken lines, with other layers of the articles such as the topsheet not displayed. The article represented is a so-called taped diaper, which comprise back ears 40 with releasable tapes 42 which can affixed to a so-called landing zone (not represented) on the front waist of the garment-facing side of the article. The article represented also comprises front ears 46 which provide a better coverage of the diaper along the front waist of the user. Of course, the core-to-backsheet gluing pattern of the invention may also be used in so-called pant diapers which have pre-sealed side edges. Some additional layers and components of the article are shown in FIG. 2, as will be discussed further below.

The absorbent article 20 comprises a front edge 10, a back edge 12, and two longitudinally extending side (lateral) edges 13, 14. The front edge 10 is the edge of the article which is intended to be placed towards the front of the user when worn, and the back edge 12 is the opposite edge. The absorbent article is notionally (i.e. virtually) divided by a longitudinal axis 80 extending from the front edge to the back edge of the article and dividing the article in two substantially symmetrical halves relative to this axis, when viewing the core in the plane formed by the longitudinal direction (y) and the transversal direction (x). The longitudinal direction extends along the length of the article, and the transversal direction is perpendicular to the longitudinal direction.

For ease of discussion, the exemplarily absorbent article is represented in a flat state extending in a transversal direction and a longitudinal direction. If some part of the article is under tension due to elasticized components, the article may be typically flattened using clamps along the periphery of the article and/or a sticky surface, so that the topsheet and backsheet can be pulled taut so as to be substantially flat. Closed articles such as training pant may be cut open along the side seams to apply them on a flat surface. Unless otherwise indicated, dimensions and areas disclosed herein apply to the article in this flat-out configuration. The article has a length L" as measured along the axis 80 from the back edge to the front edge.

The backsheet 26 may be generally rectangular as shown in FIG. 1. Shaped backsheet having a narrower waist thus forming an hour-glass shape are also known. The backsheet may then form front and back ears thus eliminating the need for additional material for these components. However this construction has other disadvantages such as having to cut-out materials resulting in waste and making it more difficult to elasticize the back ears for example.

Figure 9:
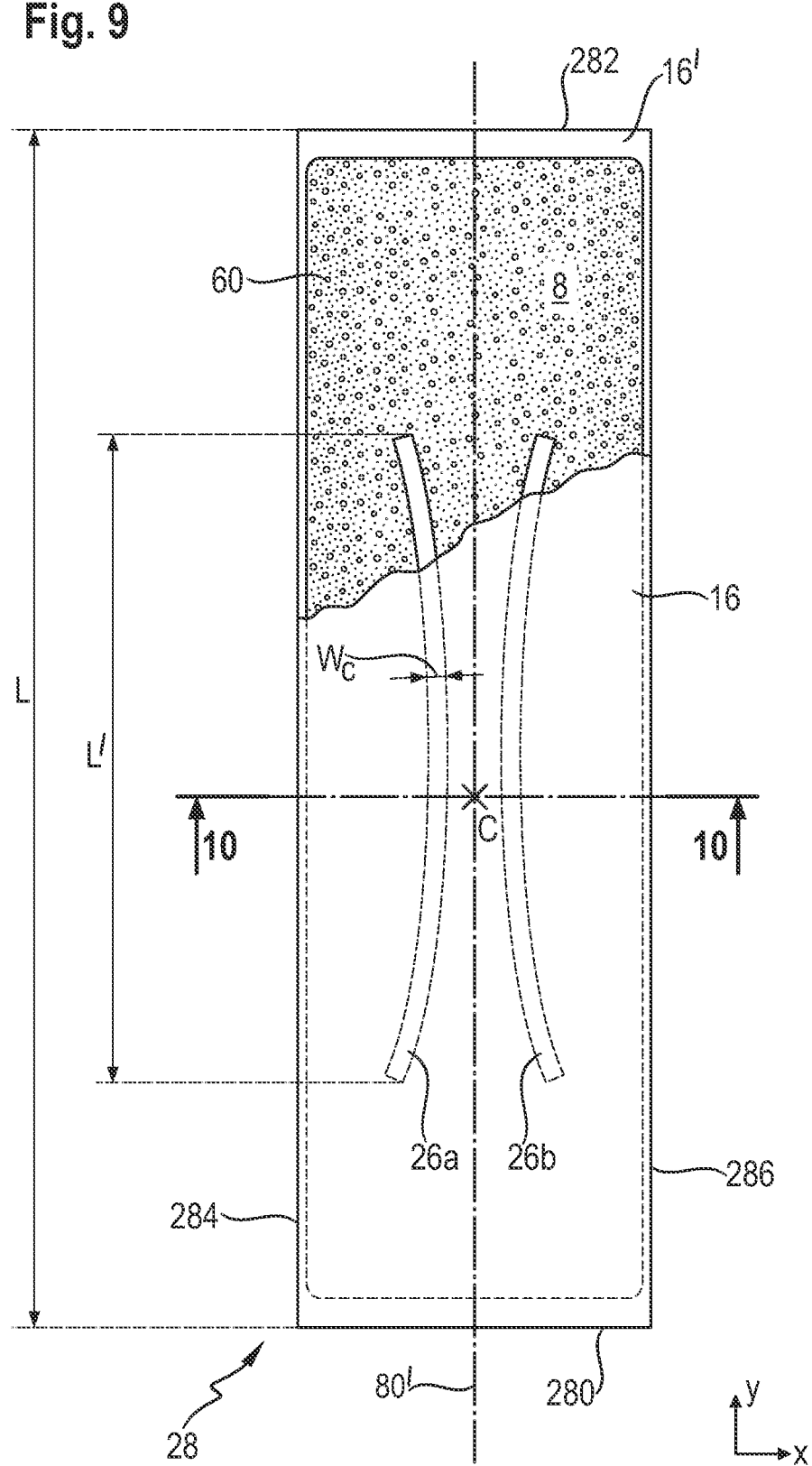
FIG. 9 is a top side view of an exemplary absorbent core in isolation.

The absorbent core 28 and its channels 26a, 26b are shown in broken lines on FIG. 1, and in isolation on FIG. 9. The channels 26a, 26b are generally longitudinally extending and may be mirror image of each other relative to the longitudinal axis. The channels may be curved, as shown in FIG. 1, but the channels may be also straight, in particular straight and orientated in the longitudinal direction. The core-to-backsheet gluing pattern will now be described in details in the following.

First Glue Application Area 100

The core-to-backsheet gluing pattern comprises a first glue, which is applied on a first glue application area 100 (herein abbreviated as "first glue area"). The first glue area 100 is at least partially present between the channels 26a, 26b, as considered from the top of the flattened article as shown in FIG. 1. Although there may be some overlap between the channels and the first glue area, it may be advantageous that the first glue area does not overlap with the channels. During use, the absorbent material around the channels may swell as they absorb a fluid and the channels will become more tridimensional. If the first glue area overlaps the channels, there is a risk that the backsheet will follow the formation of these more pronounced three-dimensional channels. This may create stress in the backsheet and lead to rupture in the backsheet. Thus it may be advantageous that the width of the first glue area is smaller than or equal to the smallest distance separating the channels areas 26a,b. The first glue area 100 may be generally aligned with and may overlap the longitudinal axis 80 of the article, for example as a slot-coated glue stripe 100 as represented in the Figures.

The dimensions of the first glue area may generally vary and depend of the type of article considered, as well as the dimensions of the channels. The channels may generally extend more in the longitudinal direction than in the transversal direction. Thus the first glue area may also extend more in the longitudinal direction. For example, the first glue area may have a length which is at least 3 times, or at least 5 times longer than it width (as projected on the y and x axis respectively). The length of the first glue area 100 may for example range from 10% to 500% of the length L' of the channels 26a,b, for example from 5 cm to 30 cm for a diaper. The width of the first glue area may also vary, for example ranging from 0.5 mm to 10 mm for a diaper.

Although not illustrated in the Figures, it is also not excluded that the first glue area may comprise a plurality of macroscopic sub-areas separated from each other. This may be the case for example if the first glue is intermittently applied to provide a series of longitudinally aligned succeeding stripes, similar to intermittent road markings. It is also possible to print the first glue with sub-areas having diverse shapes including recreational shapes such as small characters or toys, in particular if the first glue comprises a pigment so that the first glue areas is visible through the backsheet on the garment-facing side of the article. More generally, one of the glues, in particular the first glue, may comprise a pigment or other colored substance so that it is visible through the backsheet. The first glue may also not comprise a pigment or another colored substance, so that the first glue is not particularly visible through the backsheet. The first glue may be also applied in a plurality (two or more) of parallel longitudinally extending stripes. In these other examples, the dimensions of the first area as indicated above apply to the sub-areas and the spaces between these sub-areas, taken as a whole.

The first glue has a first glue application pattern within the first glue application area 100. The application pattern is dependent of the method used to apply the first glue on the substrate. The first glue may be in particular applied continuously, meaning that the glue forms a two dimensional continuous layer within the glue application area. Typically the first glue may be applied by a contact method, where the applicator directly applies the glue on top of the substrate. Advantages of direct glue application and example are listed in a publication by the Nordson company at this web address: http://www.nordson.com/en-us/divisions/adhesive-dispensing/Literature/White Paper/HoldingItTogetherBylinefromNonwovensReport.pdf. Because there is no distance or only a small distance between the nozzle and the substrate, contact deposition allows better control of the adhesive application. A typical contact applicator is a slot-coater. In slot coating, the adhesive exits the applicator through a thin, wide passageway—see FIG. 10a. Another well-known contact application technology is glue printing. These contact methods will be detailed in the process section below.

Using a contact method may typically provide the advantage of providing an accurate first glue application area 100. This may be advantageous because the distance between the channels may be relatively small, especially when the channels are curved at their closest positions relative to another. Since it may be advantageous to have no or a limited amount of glue in the areas of the channels, a contact method has the advantage of a more precise application than a non-contact method, such as adhesive spraying. A contact method also allows applying the glue continuously in the area of application. This may provide for a higher basis weight glue attachment per unit of surface, which may be an advantage as the first glue area may typically be smaller than the second glue area. The first glue area is generally limited on its side edges by the channels.

Second Glue Application Area 110

The core-to-backsheet pattern comprises a second glue on a second glue application area 110 (herein abbreviated as second glue area). This second glue area is at least partially outside the area between the channels 26a,b, in particular, the second glue may be completely absent from the area between the channels. The second glue has a different application pattern than the first glue. This allows providing the second glue area with different properties than the first glue area. As indicated previously, the first glue area 100 may require a precise deposition on a relatively narrow area at a higher basis weight of glue. The second glue application area 110 should on the other hand be able to cost-effectively cover a relatively large area, several times larger than the first glue application area, in particular the second glue area may be at least 3 times larger, or at least 5 times larger, than the first glue area. By providing for a larger area of attachment than the first glue, the second glue may ensure the overall stability of the core within the chassis of the article. The first and second glues may have the same or different compositions.

The second glue may be advantageously applied at a lower basis weight than the first glue. For example, the second glue may be applied at a basis weight which is at least 3 times, or at least 5 times lower than the basis weight of the first glue (calculated based on the respective surface of the application area for each glue). For a baby diaper, the second glue may be applied for example at a basis weight of between 0.5 to 9 gsm (grams per square meter), in particular 1-5 gsm, and the first glue at a basis weight of between 5 to 100 gsm, in particular 10-50 gsm. However the article may comprise less of the first glue in absolute amount than the second glue because of the areas difference. The total amount of first glue in an article (in particular a diaper) may for example range from 5 to 100 mg per article, in particular 10-50 mg, whereas the total amount of the first second glue may for example range from 25 to 300 mg, in particular 50-150.

Various designs for the second glue area 110 are possible. The second glue area may be unitary, as illustrated on FIGS. 1, 5-7 but it is not excluded that it comprises discrete macroscopic sub-areas or portions separated from another, as for example shown on FIG. 8 with two longitudinally extending discrete portions 1113, 1114.

The second glue area may advantageously extend, at least portion-wise, across the full length of the core and furthermore along the full length of the backsheet. These longitudinally-extending portions are indicated by reference 1113, 1114 in the Figures. This provides for full length attachment of the core to the backsheet. When the second glue area extends longitudinally beyond the core, it can further provide for attachment of the topsheet to the backsheet forward and backward of the core. The second glue application area 110 may also comprise front and back portions 1110, 1112 which are relatively large in the transversal direction, in particular that overlap or cover the entire front edge 10 and back edge 12 of the core and backsheet to provide for a stronger attachment of the core in these areas 1110, 1112. These transversally extending sub-areas may provide that the absorbent core has no free corners which may be more easily subject to delamination. In summary, the second glue area as a whole may generally have a roman II numeral shape when seen from above, as shown in FIG. 1, but other shapes are possible.

As indicated previously, the first channel and the second channel are at least partially not attached to the backsheet by the first or second glue, or otherwise. The channels may be advantageously not substantially attached by the first and second glue, or otherwise, to the backsheet. By "not substantially attached", it is meant that less than 25% of the length of each channel is attached to the backsheet. For example, only the ends of the channels may be attached by the second glue as shown on FIG. 1.

Figure 12A:
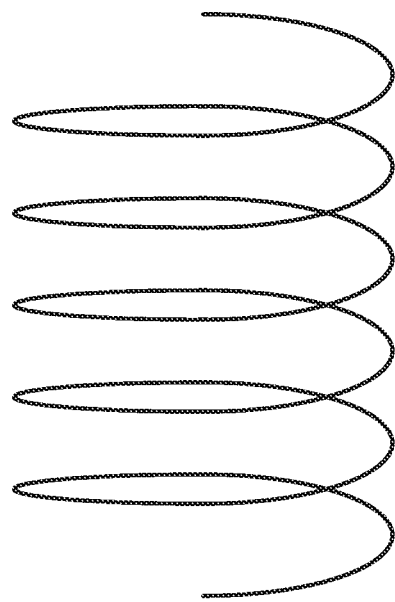
FIG. 12a,b,c illustrate three different discontinuous glue application pattern.
Figure 12B:
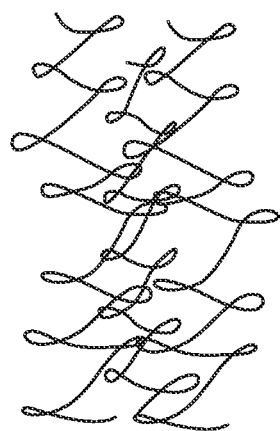
Figure 12C:
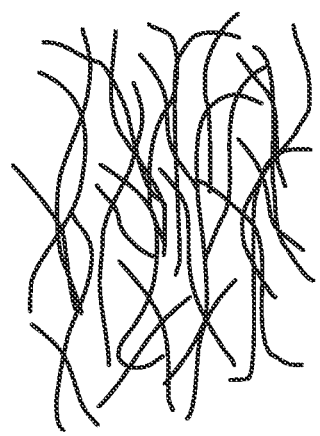

Whereas the first and second glues may have the same or different compositions, the second glue application pattern is different from the first glue application pattern. The second glue application pattern may in particular be discontinuous. By discontinuous, it is meant that the second glue does not form a continuous layer on the application area (or each sub-areas if several sub-areas are present). The second glue application pattern may for example comprise filaments, fibers or the like creating a more or less regular web with relatively large areas between the glue filaments or fibers which are not covered by glue. Examples of these patterns are illustrated in FIG. 12a-c for example (spiral, mini swirls, and random pattern respectively).

As for the first glue, the application pattern of the second glue will be typically determined by the application device used. A non-contact application method such as glue spraying is advantageous. Non-contact methods allow the coverage of relatively large areas for an economical use of glue material. The Nordson company reference document referred to above gives a good overview of usual non-contact glue applicators known in the art for gluing components of a diaper with an adhesive. The second glue application pattern may in particular comprise a plurality of spray nozzles that spray large swirls (also called "spiral" glue pattern, and illustrated on FIG. 12a), mini swirls (illustrated in FIG. 12b) or random fibrous glue patterns (illustrated in FIG. 12c). The different application devices will now be further illustrated below with reference to FIG. 11, which illustrates a process for applying the first and second glue between the backsheet and the core. The second glue pattern could also be applied by a printing glue technology which allows a better control on the pattern application but allows a well defined pattern for example less than 50% of coverage area.

Alternative Designs (FIGS. 5-8)

FIG. 1 discloses a core-to-backsheet gluing pattern wherein the first glue area is a stripe between the channels and the second glue area generally resembles roman II numeral outline.

Figure 5:
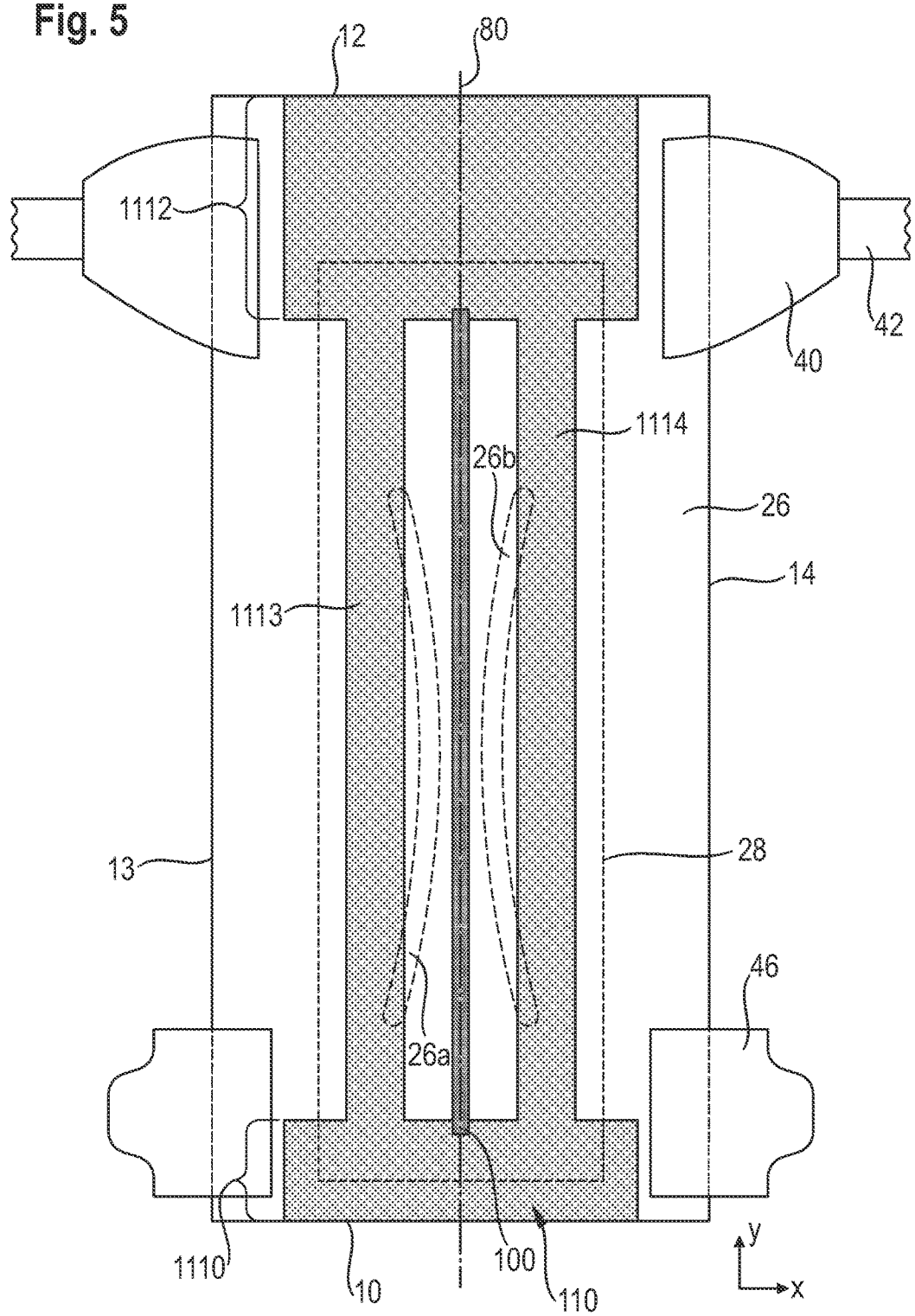
FIG. 5 shows an alternative core-to-backsheet glue pattern.
Figure 6:
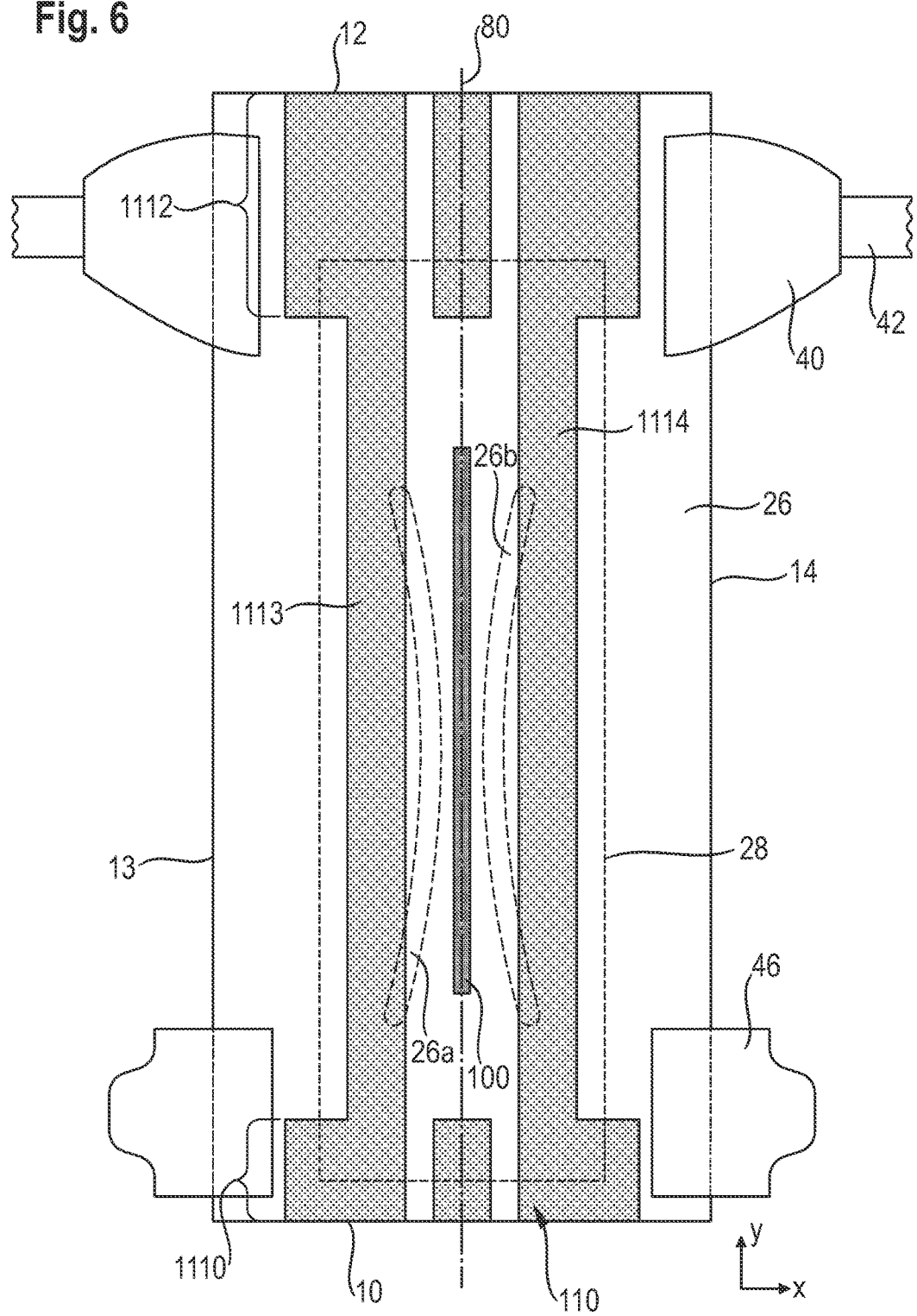
FIG. 6 shows another alternative core-to-backsheet glue pattern.

Alternative gluing pattern are of course possible, some of which are disclosed in FIGS. 5 to 8. FIG. 5 for example show an alternative pattern wherein the glue stripe of the first glue area is longer than in FIG. 1 and overlap towards its extremities with the second glue area. FIG. 6 shows another alternative design wherein the front and back portions 1110, 1112 of the second glue area are not unitary but comprise a separate central sub-area. This design allows reducing the amount of second glue used while still providing the benefits of gluing all four corners of the absorbent core to the backsheet.

Figure 7:
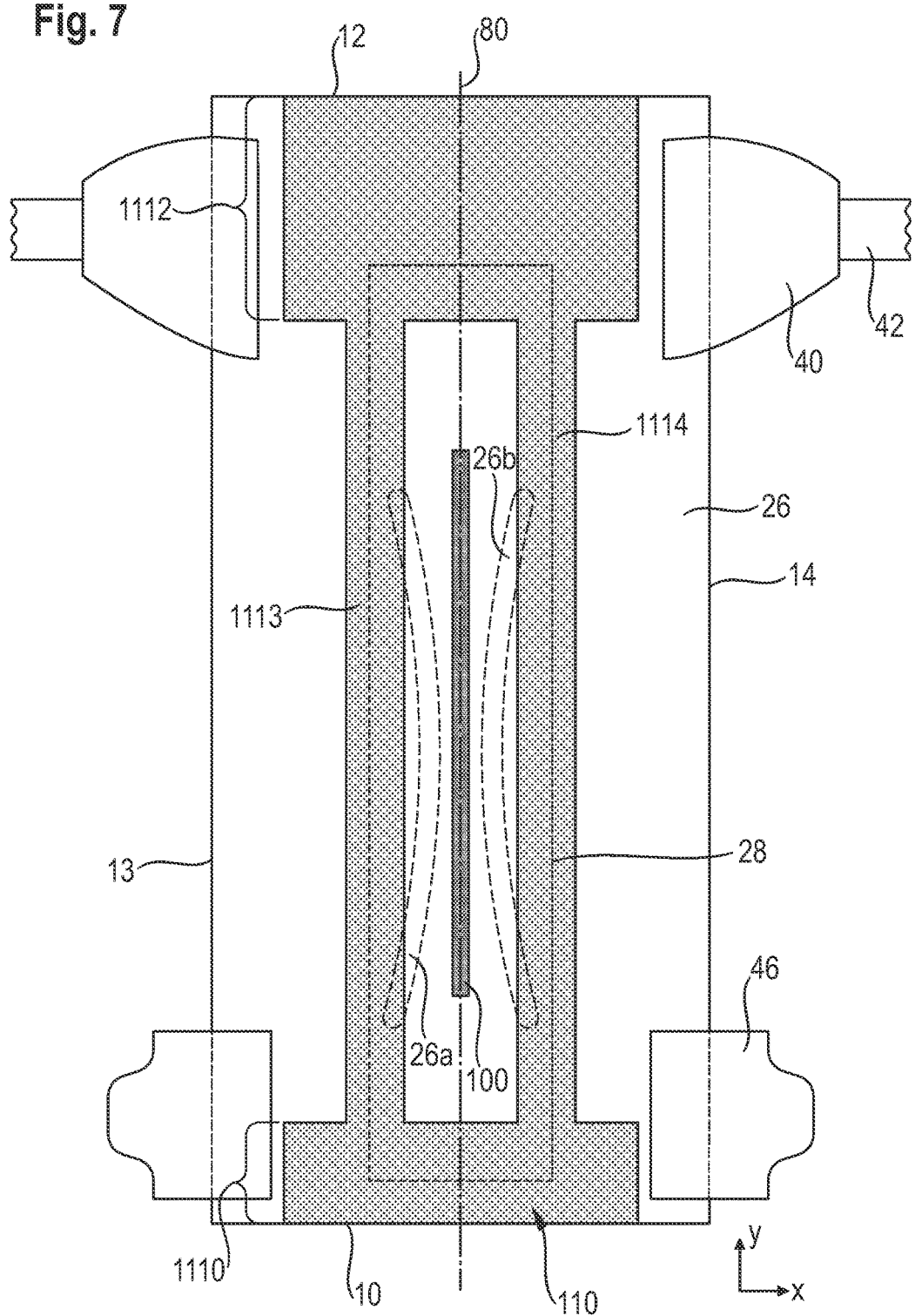
FIG. 7 shows another alternative core-to-backsheet glue pattern.

The longitudinally extending portions 1113, 1114 of the absorbent core may be typically present inwardly of the longitudinal side edges 284, 286 of the core as shown in FIG. 1, but it is not excluded that these portions 1113, 1114 overlap with the side edges 284,286 of the core, as illustrated in FIG. 7.

Figure 8:
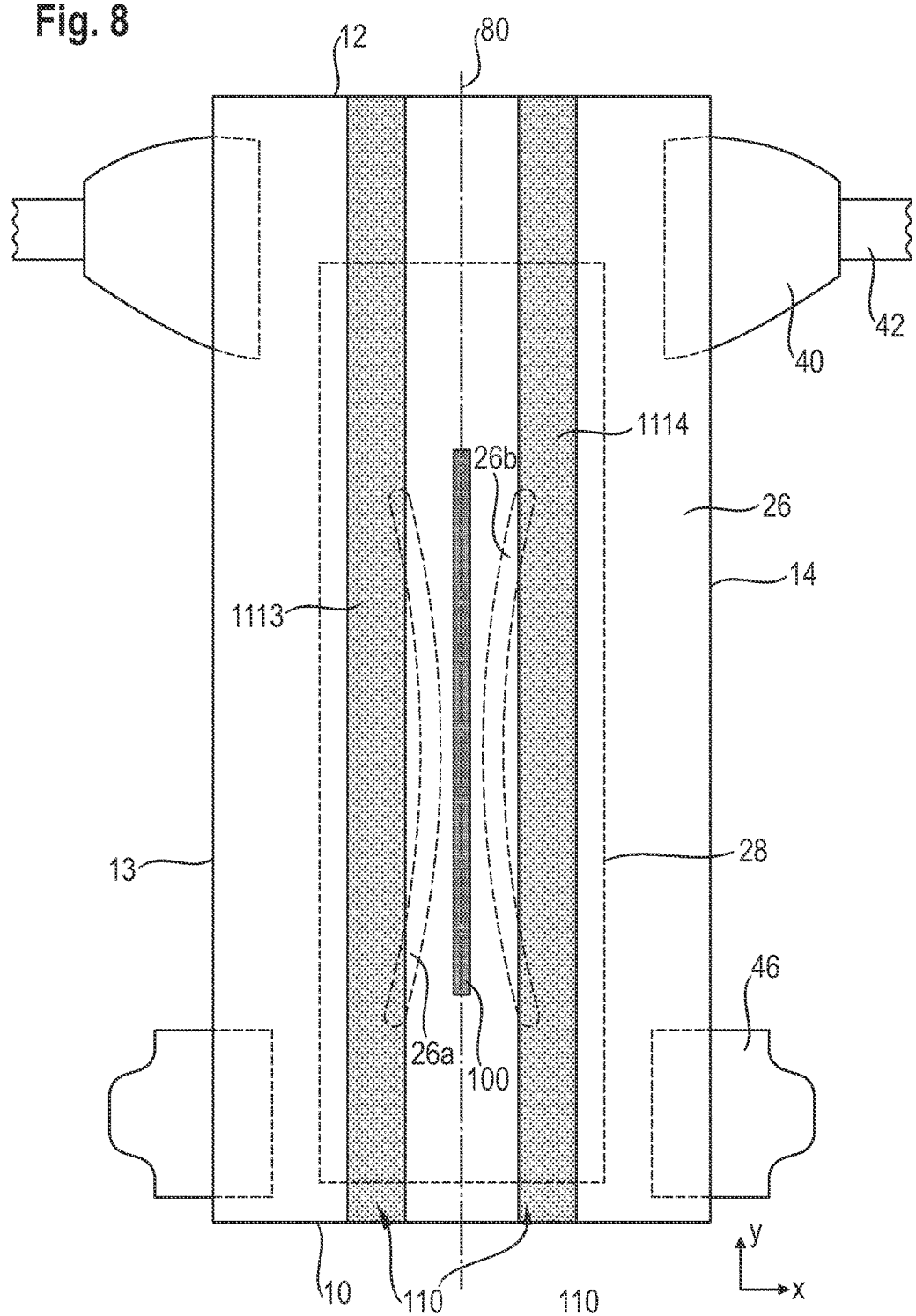
FIG. 8 shows another alternative core-to-backsheet glue pattern.

In a simplified design as illustrated on FIG. 8, the second glue area may be comprised of only two separate portions 1113, 1114 extending along the full length of the core and the backsheet. These portions may be placed inwardly of the side edges of the core (as shown in FIG. 8) or may be placed further outwardly transversally to also cover the side edges of the cores along their whole length, including the four corners of the core (not represented).

Process for Applying the First Glue and the Second Glue

The first glue and the second glue may be applied as schematically represented on FIG. 11, although other processes and variations thereof may of course be used. The process for making and assembling the rest of the absorbent article may be according any known processes in the art and will not be further detailed herein. The exemplary process of FIG. 11 shows the backsheet coming as a first continuous web feed 26 from the left side of the Figure and passing successively through two glue applicators. The first glue applicator 102 applies the first glue on the first glue application area 100. As indicated previously, this first glue applicator is advantageously a contact glue applicator, in particular for simplicity and cost a slot-coater 102 comprising a slot coating nozzle 104 (FIG. 11a) through which the slot glue is applied directly onto the backsheet. In slot coating, the adhesive exits the applicator through a thin, wide passageway—the nozzle laying the adhesive directly down on top of the substrate. The glue stripe can vary in width and pattern, depending on the application needs.

Other contact methods exist, for example as disclosed in US2011/0274834 (Brown). This document discloses a method and apparatus for the application of viscous fluids, such as adhesives, in pre-determined patterns to an advancing substrate. The fluid application apparatus may include a slot die applicator and a substrate carrier. The substrate carrier may include one or more pattern elements and may be adapted to advance the substrate past the slot die applicator as the slot die applicator discharges adhesive onto the substrate. In operation, the substrate is disposed on the substrate carrier; the substrate carrier advances the substrate past the slot opening of the slot die applicator. In turn, the substrate is intermittently compressed between the slot die applicator and the pattern surface of the pattern element. As the substrate is intermittently compressed, adhesive discharged from the slot die applicator is applied onto the substrate in an area having a shape substantially the same as a shape defined by the pattern surface. US2008/221543 (Wilkes) discloses another contact method for applying a colored hot-melt adhesive which may be used as a graphic. U.S. Pat. No. 6,033,513 (Nakamura) discloses an improved roll transfer coating method for hot melt adhesive as well as some roll transfer process of the prior art, all of which may also be used herein.

Directly after this first glue application, a second glue applicator 112 applies the second glue on the desired second glue application area 110 according to the second glue application pattern. The second glue applicator may be in particular a non-contact applicator. The second glue applicator 112 may comprise a plurality of nozzles 114b, 114c installed in parallel as represented on FIGS. 11b and 11c. In the example described, the second applicator 112 comprises 6 nozzles which can be independently controlled and turned on and off to form the desired second glue area such as the roman numeral II of FIGS. 1, 5 and 7. In another example, the second applicator device may comprise 5 such nozzles, with the third nozzles separated by a gap from the two neighboring nozzles, to provide for a second glue application are as shown on FIG. 6. In another example, the second applicator 102 may for example comprise only two nozzles on each side of the longitudinal axis to provide a second glue application area as shown on FIG. 8.

The individual spray nozzles of the second glue applicator may be of any type known in the art. In a first applicator example 112b, the nozzles may be for example as available from Nordson under the designation "CF applicator". These nozzles each deliver a single large swirl (also called spiral) from each nozzle 114b, as illustrated on FIG. 12a. The width of such large spiral may for example range from 10 mm to 30 mm. In the case of 6 such nozzles 114b installed in parallel, by intermittently turning on and off some of the nozzles (for example nozzles 1, 3, 4 and 6) and leaving two nozzles (2 and 5) continuously on, a roman II pattern can be repeatedly applied on an substrate such as the backsheet web feed. The same principle of placing in parallel a plurality of nozzles to apply the desired pattern works for other applicators. The second glue may be in particular applied by an applicator 114c comprising several nozzle units 114c with a plurality of so-called mini-swirl nozzles, for example available from Nordson under the "Summit" designation. Each of these nozzle units 114c has a plurality, in particular three as represented for nozzle 114c, of sub-nozzles that together distribute several small swirls of adhesive (as illustrated on FIG. 12b). Each unit may apply a plurality of swirls having together the same width as indicated previously for one large swirl/spiral pattern. These nozzle units may also be independently turned on and off to provide the desired area of coverage. Mini-swirls can be used at a faster speed than large swirl/spiral and have a better edge definition, while not being as precise as slot application. Of course any other known spraying nozzle type may be used, for example nozzle spraying a random pattern of glue, such as those supplied by Nordson under the "Signature" spray nozzle designation. These nozzles may produce random pattern of glue in fibrous form. Although randomly sprayed, the adhesive filaments may appear as being generally longitudinally aligned (see illustration of FIG. 12c) due to the movement of the web at high speed. An air flow may be used in conjunction with a spray nozzle to direct or disperse the glue filaments.

In addition, the second glue application area may advantageously extend forwards and backwards of the absorbent core to provide for extended areas of gluing of the backsheet with the topsheet for example. The front and back glue portions 1110, 1112 which may be relatively large to cover the front and back edges of the core may be separated by an intermediate area with a lesser amount of second glue coverage. The intermittently functioning nozzles (numbers 1, 3, 4 and 6 in this example) may be turned off for the intermediate area between the areas 1110, 1112. This allows material savings, as well as giving more freedom of movement of the core relative to the backsheet in this intermediate area. The intermittently functioning nozzles may be switched on and off only once for each individual core-to-backsheet gluing pattern. For example, the intermittent nozzles are switched on to form the larger back second glue portion 1112, and remain on to form the front larger second glue portion 1110 of the following gluing pattern, before being switched off for the intermediate middle region of this following gluing pattern.

It may be advantageous, as represented, to apply the first glue before the second glue, in particular when the first glue is applied with a contact applicator and second glue is applied with a non-contact applicator. Otherwise, there could be a risk of smearing the second glue on the contact applicator of the first glue. Similarly, it may be advantageous to apply the first and second glue onto the backsheet rather than the absorbent core, as the backsheet is a continuous web of material that will be typically easier to handle and can provide for a continuous application of the second glue over two succeeding core-to-backsheet gluing pattern.

After the glues have been applied, the feed of absorbent cores, as shown coming from the right, is then synchronized with the glue application patterns of the backsheet so that when the backsheet and absorbent core are brought in face-to-face contact with some pressure, they are attached by the first glue and second glue. The feed of absorbent cores may be supported on a continuous substrate which may be a component of the article. The supporting substrate for the absorbent cores may be in particular the remaining components of the article which have been pre-assembled on the line, with the topsheet 24 being the largest of these components on which the other have been assembled. The articles are then individualized for example by die cutting. Of course, other glues or attachment means, such as a chassis side slots on each of the longitudinal edges 13, 14 may be added to form the longitudinal seals between the backsheet and the topsheet and/or barrier leg cuffs of the final articles. These additional glues or other attachment means are not represented in the Figures for simplicity but may be as is known from any conventional absorbent articles.

Composition of the First Glue and the Second Glue

The first glue and second glue may be any type of glue known in the art and suitable to be applied according to the desired application pattern. The first glue and the second glue composition may be the same or different. In particular, any kind of thermoplastic hot-melt adhesives used in the field of absorbent article making may be suitable. Such an adhesive generally includes one or more polymers to provide cohesive strength (e.g., aliphatic polyolefins such as ethylene-propylene copolymers, polyetheramides, polyetheresters, and combinations thereof; ethylene vinyl acetate copolymers; styrene-butadiene or styrene-isoprene block copolymers; etc.), a resin or analogous material (sometimes called a tackifier) to provide adhesive strength (e.g., hydrocarbons distilled from petroleum distillates; rosins and/or rosin esters; terpenes derived, for example, from wood or citrus, etc.); and optional waxes, plasticizers or other materials to modify viscosity (e.g., mineral oil, polybutene, paraffin oils, ester oils, and the like), and/or other additives including, but not limited to, antioxidants or other stabilizers. Further information about hotmelt adhesive chemistry is discussed below for the fibrous thermoplastic adhesive layer that may be used in the absorbent core.

Exemplary suitable commercial adhesives for the first and/or second glue are available from Fuller under reference number 1286 or 1358, or from National Starch & Chemical under reference number DM 526, DM538 or DM3800.

General Description of the Absorbent Core 28

As used herein, the term "absorbent core" refers to a component of the absorbent article which comprises an absorbent material enclosed in a core wrap. As used herein, the term "absorbent core" does not include the topsheet, the backsheet and (if present) an acquisition-distribution layer or multilayer system, which is not integral part of the absorbent core, in particular which is not placed within the core wrap. The absorbent core is typically the component of an absorbent article that has the most absorbent capacity of all the components of the absorbent article and which comprises all, or at least the majority of, superabsorbent polymer (SAP). The core may consist essentially of, or consist of, the core wrap, the absorbent material and adhesives. The terms "absorbent core" and "core" are herein used interchangeably.

An exemplary core 28 that can be used in the invention is represented in FIGS. 9-10. The absorbent cores can typically be laid flat on a surface as shown on FIG. 9. The absorbent cores may also be typically thin and conformable, so that they can also be laid on a non-flat surface for example a drum during their making process or stored as a continuous roll of stock material before being converted into an absorbent article. For ease of discussion, the exemplarily absorbent core of FIG. 9 is represented in a flat state and extending in a transversal direction and a longitudinal direction. Unless otherwise indicated, dimensions and areas disclosed herein apply to the core in this flat-out configuration. The same applies to the absorbent article in which the core is integrated.

The absorbent core can typically be generally rectangular with a width W in the transversal direction and a length L in the longitudinal direction as measured from edge to edge, including the region of the core wrap which does not enclose the absorbent material, in particular at the front and back ends 280, 282, which may be sealed. In case the core is not rectangular, the maximum dimension measured along the transversal and longitudinal direction can be used to report the length and width of the core. The width and length of the core may vary depending on the intended usage. For baby and infant diapers, the width L may for example in the range from 40 mm to 200 mm and the length from 100 mm to 500 mm, as measured along the longitudinal axis 80' of the core. The longitudinal axis 80' of the core may be contiguous with the longitudinal axis 80 of the article. The article further comprises a liquid permeable topsheet 24 and a liquid impermeable backsheet 25 with the absorbent core 28 positioned between the topsheet and the backsheet.

The absorbent core comprises a front edge 280, a back edge 282 and two longitudinally extending side edges 284, 286 joining the front edge and the back edge. The front edge of the core is the edge of the core intended to be placed towards the front edge of the absorbent article. Typically the absorbent material 60 of the core may be advantageously distributed in somewhat higher amount towards the front edge than towards the back edge as more absorbency is typically required towards the front half of the article. Typically the front and back edges 280, 282 of the core may be shorter than the side edges 284, 286 of the core. The absorbent core may also comprise a top side 288 and a bottom side 290. The top side of the core is the side placed or intended to be placed towards the topsheet 24 of the article and the bottom side is the side placed or intended to be placed towards the backsheet 25 in the finished article. The top side of the core wrap is typically more hydrophilic than the bottom side.

The transversal axis of the core (herein also referred to as "crotch line"), is defined as the virtual line perpendicular to the longitudinal axis and passing through the crotch point C of the core. The crotch point C is defined as the point of the absorbent core placed at a distance of 0.45 of L from the front edge of the absorbent core, L being the length of the core as measured from the front edge 280 in direction of the back edge 282, as shown on FIG. 9.

The following will provide an exemplary description of possible core components. Further details are described for example in WO2012/170778 (Rosati et al.), WO2014/93311A1 (Arizti et al), WO2014/093310 (Ehrnsperger et al.), which disclose absorbent structures that comprise superabsorbent polymers, optionally a cellulosic material, and at least a pair of substantially longitudinally extending channels.

Core Wrap 16, 16'

The core wrap may comprise a first substrate 16 generally forming the top side of the core and a second substrate 16' generally forming the bottom side of the core wrap. The first and second substrates may be formed by two different materials, as shown in FIG. 10, but any other known core wrap constructions may also be used, for example wherein the core wrap is formed of a single material with one single longitudinal seal. The first and second substrates can be attached by gluing or otherwise to form at least one C-wrap seal 72 along each of the side edges 284, 286 of the core. The first and second substrates may be a nonwoven web, such as a laminate comprising spunbond ("S") or meltblown ("M") layer. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US 2011/0268932 A1, US 2011/0319848 A1 and US 2011/0250413 A1. The bottom substrate 16' may be inherently hydrophobic but air-permeable, and the top substrate 16 may be hydrophillically treated. There may be a seal along the front edge 282 and back edge 280 of the core wrap.

Combining the auxiliary glue layer with a C-wrap seal along at least one and preferably two longitudinal edges of the core, and optionally a further fibrous adhesive web (not represented), can provide an immobilization of the absorbent material in dry and wet state. The absorbent core may in general advantageously achieve an SAP loss of no more than about 70%, 60%, 50%, 40%, 30%, 20%, or 10% according to the Wet Immobilization Test described in US2010/0051166A1.

Absorbent Material 60

The absorbent material in the core can comprise a relatively high proportion of superabsorbent polymer (herein abbreviated as "SAP") enclosed within the core wrap. The SAP content may represent in particular at least 85%, 90%, 95% and up to 100%, of superabsorbent polymer by weight of the absorbent material. The absorbent material may in particular comprise no or only small amount of cellulose fibers, such as less than 20%, in particular less than 10%, 5% or even 0% of cellulose fibers by weight of the absorbent material. The absorbent material may thus advantageously consist or consist essentially of SAP. The SAP may be typically in particulate forms (superabsorbent polymer particles), but it not excluded that other form of SAP may be used such as a superabsorbent polymer foam for example. The absorbent core may thus be relatively thin, in particular thinner than conventional cores comprising cellulosic fibers. In particular, the caliper of the core (before use) as measured at the crotch point (C) or at any other points of the surface of the core according to the Core Caliper Test as described herein may be from 0.25 mm to 5.0 mm, in particular from 0.5 mm to 4.0 mm.

The term "superabsorbent polymer" refers herein to absorbent materials, which may be cross-linked polymer, and that can typically absorb at least 10 times their weight of an aqueous 0.9% saline solution as measured using the Centrifuge Retention Capacity (CRC) test (EDANA method WSP 241.2-05E). The SAP may in particular have a CRC value of more than 20 g/g, or more than 24 g/g, or of from 20 to 50 g/g, or from 20 to 40 g/g, or 24 to 30 g/g. The fluid permeability of a superabsorbent polymer can be quantified using its Urine Permeability Measurement (UPM) value, as measured in the test disclosed European patent application EP2,679,209. The UPM of the SAP may for example be of at least $10\times10^{-7}$ cm$^3$·sec/g, or at least $30\times10^{-7}$ cm$^3$·sec/g, or at least $50\times10^{-7}$ cm$^3$·sec/g, or more, e.g. at least 80 or $100\times10^{-7}$ cm$^3$·sec/g.

Absorbent Material Deposition Area 8

The absorbent material 60 defines an absorbent material deposition area 8, as seen from above within the plane of the core. The absorbent material deposition area 8 is defined by the periphery of the layer of absorbent material 60 within the core wrap, as seen from the top side of the absorbent core as shown on FIG. 9, and comprises the channel areas 26a,b encompassed within. The absorbent material deposition area 8 can be generally rectangular, for example as shown in FIG. 9, but other shapes can also be used such as a "T" or "Y" or "sand-hour" or "dog-bone" shape. In particular the deposition area may show a tapering along its width at the crotch region of the core. In this way, the absorbent material deposition area may have a relatively narrow width in an area of the core intended to be placed in the crotch region of the absorbent article. This may provide for example better wearing comfort.

Channels 26a,b

The absorbent cores comprise at least two channels 26a,b (also referred to herein as "channel areas"). The term "channel" designates a longitudinally extending area of the core comprising less absorbent material than the surrounding areas so that an insulting fluid can be quickly distributed along the channel towards the front and back of the core. The channels may be in particular substantially free of absorbent material. By "substantially free" it is meant that in each of these areas the basis weight of the absorbent material is at least less than 25%, in particular less than 20%, less than 10%, of the average basis weight of the absorbent material in the rest of the absorbent material deposition area of the core. In particular there can be no absorbent material in these areas 26ab. Minimal amount such as involuntary contaminations with absorbent material particles that may occur during the making process are not considered as absorbent material. The channels 26 are advantageously surrounded by the absorbent material, when considering the plane of the core, which means that the areas 26 do not extend to any of the edges of the deposition area 8 of the absorbent material 60.

The top layer 16 and the bottom layer 16' of the core wrap may be bonded to each other through these channel 26a,b. The bond 27 between the substrates in these area may be at least partially formed by an auxiliary glue 71 applied directly to the inner surface of at least one of the substrate, but other bonding methods are not excluded. This bonding allows the channels 26 to form more pronounced three-dimensional channels 26' as the absorbent material swells when it absorbs a liquid such as urine. Examples of channels according to the invention are described in details for example in WO2012/170778 (Rosati et al.), WO2014/93311A1 (Arizti et al), WO2014/093310 (Ehrnsperger et al.) which disclose absorbent structures that comprise superabsorbent polymers, optionally a cellulosic material, and at least a pair of substantially longitudinally extending channels.

When the absorbent material 60 swells upon absorbing a liquid, the core wrap bonds 27 remain at least initially attached in the channel areas 26. The absorbent material 60 swells in the rest of the core when it absorbs a liquid, so that the core wrap forms one or more pronounced channels along the core wrap bond 27. These channels are three dimensional and can serve to distribute an insulting fluid along their length to a wider area of the core. They may provide a quicker fluid acquisition speed and a better utilization of the absorbent capacity of the core.

The absorbent core 28 comprise at least a first and second channels 26ab disposed on each side of the longitudinal axis 80'. It is not excluded that the core may also comprise more than two channels. Shorter channel areas substantially free of absorbent material may also be present, for example in the back region or the front region of the core, as seen for example in the Figures of WO2012/170778.

The channels may extend substantially longitudinally, which means typically that each area extends at least as much in the longitudinal direction (y) than in the transversal direction (x), and typically at least twice as much in the longitudinal direction than in the transverse direction (as measured after projection on the respective axis). The channels 26 may have a length L' projected on the longitudinal axis 80 of the core that is at least 10% of the length L of the absorbent core, in particular from 20% to 80%. The channels may have an area substantially free of absorbent material having a width We along at least part of their length which is at least 2 mm, or at least 3 mm or at least 4 mm, up to for example 20 mm, or 16 mm or 12 mm. The width We may be constant through substantially the whole length or may vary along the length of the channels.

The channels 26 may be curved as shown in the Figures but they may be also straight and parallel to the longitudinal axis. It may be advantageous that there is no channels that coincide with the longitudinal axis 80' of the core. When present as a pair of channels 26a,b, these may be spaced apart from one another over their whole longitudinal dimension. The smallest spacing distance may be for example at least 5 mm, or at least 10 mm, or at least 16 mm.

Process for Making the Core

The absorbent material 60 may be deposited on any of the substrates 16, 16' using known techniques. In particular the SAP printing technology as disclosed for example in US2006/024433 (Blessing), US2008/0312617 and US2010/0051166A1 (both to Hundorf et al.), which allow relatively precise deposition of SAP at relatively high speed may be used. This technique uses a transfer device such as a printing roll to deposit SAP onto a substrate disposed on a grid of a support which may include a plurality of cross bars extending substantially parallel to and spaced from one another. Channel areas 26 substantially free of absorbent material can be formed for example by modifying the pattern of the grid and receiving drums so that no SAP is applied in the selected areas, as exemplary disclosed in US2012/0312491 (Jackels). This technology allows high-speed and precise deposition of SAP on a substrate in particular to provide one or more area(s) 26 substantially free of absorbent material surrounded by absorbent material. US2014/027066 (Jackels) further discloses specific raised strips and mating strips on the equipment for bonding the core substrates through the channel areas.

The absorbent material may be substantially continuously distributed in the deposition area 8. By "substantially continuous" it is meant that at least 50%, or at least to 70% and up to 100% of the deposition area comprises a continuous layer of absorbent material as seen from the top side of the core. The absorbent material may be for example applied as a single continuous layer on one of the substrate, the layer thus directly forming the material deposition area 8. A continuous layer of absorbent material, in particular of SAP, may also be obtained by combining two absorbent layers having matching discontinuous absorbent material application pattern wherein the resulting layer is substantially continuously distributed across the absorbent material deposition area, as exemplarily taught in US2008/0312622A1 (Hundorf).

Microfiber Glue

The absorbent core 28 may also comprise a fibrous thermoplastic adhesive material, to further immobilize the absorbent material 60 during the making process of the core and usage of the article. The fibrous thermoplastic adhesive material may be in particular useful to immobilize a dual layers of absorbent material to their respective substrate 16, 16'. Each of these absorbent layers may comprise land areas separated by junction areas and the fibrous thermoplastic adhesive material may then be at least partially in contact with the absorbent material in the land areas and at least partially in contact with the substrate layer 16, 16' in the junction areas. This imparts an essentially three-dimensional net-like structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material in the land areas, and thereby immobilizes this absorbent material. The fibrous adhesive may be for example sprayed on an absorbent layer after it has been deposited on its substrate during the core making process.

The fibrous thermoplastic adhesive material may typically have a molecular weight (Mw) of more than 10,000 and a glass transition temperature (Tg) usually below room temperature or $-6°$ C.$<Tg<16°$ C. Typical concentrations of the polymer in a hotmelt are in the range of about 20% to about 40% by weight. The thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

The tackifying resin may exemplarily have a Mw below 5,000 and a Tg usually above room temperature, typical concentrations of the resin in a hotmelt are in the range of about 30 to about 60%, and the plasticizer has a low Mw of typically less than 1,000 and a Tg below room temperature, with a typical concentration of about 0 to about 15%.

The thermoplastic adhesive used for the fibrous layer preferably has elastomeric properties, such that the web formed by the fibers on the SAP layer is able to be stretched as the SAP swell. Exemplary elastomeric, hotmelt adhesives include thermoplastic elastomers such as ethylene vinyl acetates, polyurethanes, polyolefin blends of a hard component (generally a crystalline polyolefin such as polypropylene or polyethylene) and a Soft component (such as ethylene-propylene rubber); copolyesters such as poly(ethylene terephthalate-co-ethylene azelate); and thermoplastic elastomeric block copolymers having thermoplastic end blocks and rubbery mid blocks designated as A-B-A block copolymers: mixtures of structurally different homopolymers or copolymers, e.g., a mixture of polyethylene or polystyrene with an A-B-A block copolymer; mixtures of a thermoplastic elastomer and a low molecular weight resin modifier, e.g., a mixture of a styrene-isoprenestyrene block copolymer with polystyrene; and the elastomeric, hot-melt, pressure-sensitive adhesives described herein. Elastomeric, hot-melt adhesives of these types are described in more detail in U.S. Pat. No. 4,731,066 (Korpman).

The thermoplastic adhesive material fibers may exemplarily have an average thickness of about 1 to about 50 micrometers or about 1 to about 35 micrometers and an average length of about 5 mm to about 50 mm or about 5 mm to about 30 mm. The auxiliary glue may improve the adhesion of the thermoplastic adhesive material to the substrate. The fibers adhere to each other to form a fibrous layer, which can also be described as a mesh. This is further detailed in the Rosati and Jackels references previously indicated.

General Description of the Absorbent Article 20

Figure 3:
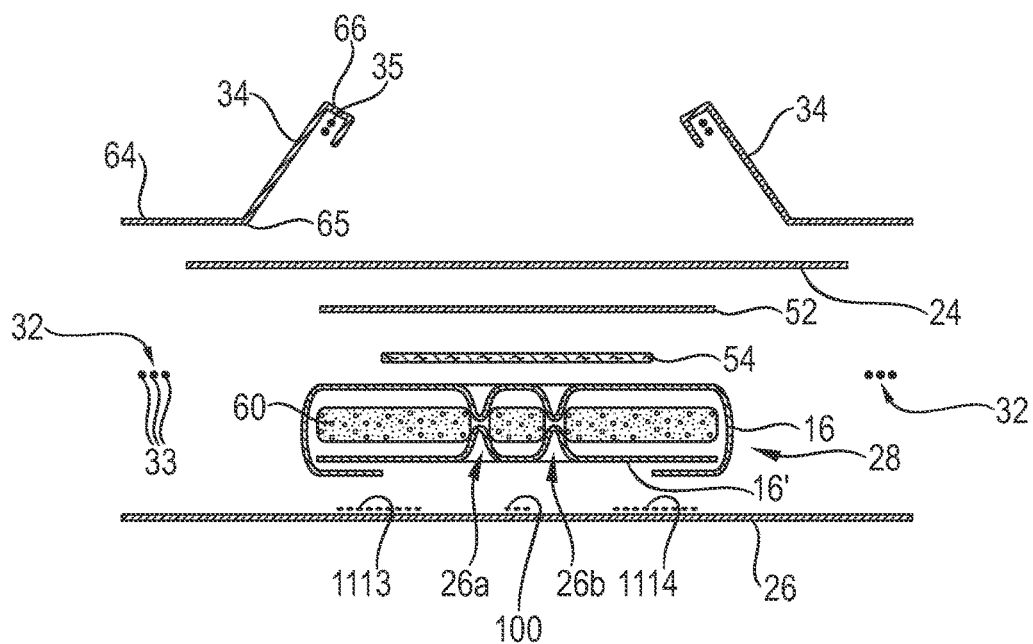
FIG. 3 shows a schematic cross-section of an absorbent article as in FIG. 2 in the center of the article.
Figure 4:
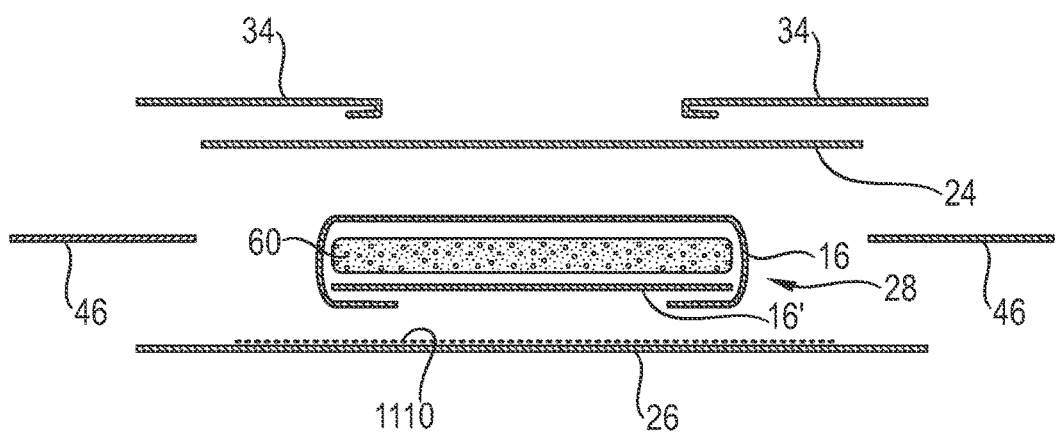
FIG. 4 shows a schematic cross-section of the absorbent article as in FIG. 2 towards the front edge of the article.

The absorbent article 20 comprises a liquid permeable topsheet 24, a liquid impermeable backsheet 25 and an absorbent core 28 according to the invention between the topsheet 24 and the backsheet 25. Some typical components of a baby taped diaper 20 are further represented in FIG. 2 in exploded view, and in cross-section view in FIGS. 3-4. Typically all components will be attached to the other neighboring components by glue, heat and pressure bonding, or otherwise, but only the core-to-backsheet gluing pattern is represented in these Figures for readability. The absorbent article may also comprise further typical components such as an acquisition layer 52 and/or a distribution layer 54, elasticized gasketing cuffs 32 within the chassis and partially upstanding barrier leg cuffs 34. The Figures also show other typical taped diaper components such as a fastening system comprising fastening tabs 42 attached towards the back edge 12 of the article and cooperating with a landing zone towards the front edge 10 of the article. The absorbent article may also comprise other typical components, which are not represented in the Figures, such as a back elastic waist feature, a front elastic waist feature, transverse barrier cuffs, a lotion application, a wetness indicator that reacts with urine such as a pH indicator which may be incorporated in the first or second glues, in particular the first glue, etc.

The topsheet 24, the backsheet 25, the absorbent core 28 and the other article components may be assembled in a variety of well-known configurations, in particular by gluing and/or heat embossing. Exemplary diaper assemblies are for example generally described in U.S. Pat. Nos. 3,860,003, 5,221,274, 5,554,145, 5,569,234, 5,580,411, and 6,004,306. The absorbent article is preferably thin. The article may be advantageously thin at the intersection of the longitudinal and transversal axes, for example with a caliper of from 1.0 mm to 8.0 mm, in particular from 1.5 mm to 6.0 mm, as measured using the Absorbent Article Caliper Test described below.

These and other components of the article will now be discussed in more detail.

Topsheet 24

The topsheet 24 forms at least a part of wearer-facing side of the absorbent article and is directly in contact with the wearer's skin. The topsheet 24 can be joined to the backsheet 25, the absorbent core 28 and/or any other layers as is known in the art (as used herein, the term "joined" encompasses configurations whereby an element is directly secured to another element by affixing the element directly to the other element, and configurations whereby an element is indirectly secured to another element by affixing the element to intermediate member(s) which in turn are affixed to the other element). Usually, the topsheet 24 and the backsheet 25 are joined directly to each other in some locations (e.g. on or close to the periphery of the article) and are indirectly joined together in other locations by directly joining them to one or more other elements of the article 20.

The topsheet 24 is preferably compliant, soft-feeling, and non-irritating to the wearer's skin. Further, at least a portion of the topsheet 24 is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. Typical diaper topsheets have a basis weight of from about 10 to about 28 gsm, in particular between from about 12 to about 18 gsm but other basis weights are possible.

Suitable formed film topsheets are also described in U.S. Pat. Nos. 3,929,135, 4,324,246, 4,342,314, 4,463,045, and 5,006,394. Other suitable topsheets may be made in accordance with U.S. Pat. No. 4,609,518 and U.S. Pat. No. 4,629,643. Such formed films are available from The Procter & Gamble Company of Cincinnati, Ohio as "DRI-WEAVE" and from Tredegar Corporation, based in Richmond, Va., as "CLIFF-T".

Any portion of the topsheet may be coated with a lotion as is known in the art. Examples of suitable lotions include those described in U.S. Pat. Nos. 5,607,760, 5,609,587, 5,643,588, 5,968,025 and 6,716,441. The topsheet 24 may also include or be treated with antibacterial agents, some examples of which are disclosed in WO 95/24173. Further, the topsheet, the backsheet or any portion of the topsheet or backsheet may be embossed and/or matte finished to provide a more cloth like appearance.

The topsheet 24 may comprise one or more apertures to ease penetration of exudates there-through, such as urine and/or feces (solid, semi-solid, or liquid). Examples of apertured topsheet are disclosed in U.S. Pat. No. 6,632,504. WO 2011/163582 also discloses suitable colored topsheet having a basis weight of from 12 to 18 gsm and comprising a plurality of bonded points. Each of the bonded points has a surface area of from 2 $mm^2$ to 5 $mm^2$ and the cumulated surface area of the plurality of bonded points is from 10 to 25% of the total surface area of the topsheet.

Backsheet 25

The backsheet 25 is generally that portion of the absorbent article 20 which forms the majority of the external surface of the article when worn by the user. The backsheet 25 is positioned towards the bottom side 290 of the absorbent core 28 and prevents the exudates absorbed and contained therein from soiling articles such as bed sheets and undergarments. The backsheet 25 is typically impermeable to liquids (e.g. urine). The backsheet 25 may for example be or comprise a thin plastic film, on the exterior surface of which a thin non-woven may be attached to improve the feel to the touch. Exemplary backsheet films include those manufactured by Tredegar Corporation, based in Richmond, Va., and sold under the trade name CPC2 film. Other suitable backsheet materials may include breathable materials which permit vapors to escape from the article 20 while still preventing exudates from passing through the backsheet 25. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097. Some breathable composite materials are described in greater detail in WO 95/16746 (E. I. DuPont), U.S. Pat. No. 5,938,648 (LaVon et al.), U.S. Pat. No. 4,681,793 (Linman et al.), U.S. Pat. No. 5,865,823 (Curro), U.S. Pat. No. 5,571,096 (Dobrin et al.) and U.S. Pat. No. 6,946,585 (London Brown).

Acquisition and Distribution Layers 52, 54

The absorbent articles of the invention may comprise an acquisition layer 52, a distribution layer 54, both, or a single layer having both functions of acquiring and distributing the fluid. Typically, these layers do not comprise SAP as this may slow the acquisition and distribution of the fluid. The prior art discloses many type of acquisition-distribution system, see for example WO 2000/59430 (Daley), WO 95/10996 (Richards), U.S. Pat. No. 5,700,254 (McDowall), WO 02/067809 (Graef).

The function of an acquisition layer is to quickly acquire the fluid away from the topsheet so as to provide a good dryness for the wearer. The acquisition layer is typically placed directly under the topsheet. If present, the distribution layer may be at least partially disposed under the acquisition layer. The acquisition layer may typically be or comprise a non-woven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round or round and hollow PET staple fibers (50/50 or 40/60 mix of 6 denier and 9 denier fibers). An exemplary binder is a butadiene/styrene latex. Nonwovens have the advantage that they can be manufactured outside the converting line and stored and used as a roll of material. Further useful nonwovens are described in U.S. Pat. No. 6,645,569 (Cramer et al.), U.S. Pat. No. 6,863,933 (Cramer et al.), U.S. Pat. No. 7,112,621 (Rohrbaugh et al.), US 2003/148684 (Cramer et al.) and US 2005/008839 (Cramer et al.).

The acquisition layer may be stabilized by a latex binder, for example a styrene-butadiene latex binder (SB latex). Processes for obtaining such latices are known, for example, from EP 149880 (Kwok) and US 2003/0105190 (Diehl et al.). In certain embodiments, the binder may be present in the acquisition layer 52 in excess of about 12%, about 14% or about 16% by weight. SB latex is available under the trade name GENFLO™ 3160 (OMNOVA Solutions Inc.; Akron, Ohio).

A distribution layer 54 may also be present. The function of a distribution layer is to spread the insulting fluid liquid over a larger surface within the article so that the absorbent capacity of the core can be more efficiently used. Typically the distribution layer is made of a nonwoven material based on synthetic or cellulosic fibers and having a relatively low density. The density of the distribution layer may vary depending on the compression of the article, but may typically range from 0.03 to 0.25 g/cm$^3$, in particular from 0.05 to 0.15 g/cm$^3$ measured at 0.30 psi (2.07 kPa). The distribution layer 54 may also be a material having a water retention value of from 25 to 60, preferably from 30 to 45, measured as indicated in the procedure disclosed in U.S. Pat. No. 5,137,537. The distribution layer 54 may typically have an average basis weight of from 30 to 400 g/m$^2$, in particular from 100 to 300 g/m$^2$. As shown in FIG. 2, the distribution layer may be rounded towards the back of the article. The distribution layer may be also profiled so that its basis weight towards the back of the article is lower than towards the front.

The distribution layer may for example comprise at least 50% by weight of crosslinked cellulose fibers. The crosslinked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf). The crosslinked cellulosic fibers provide higher resilience and therefore higher resistance against the compression in the product packaging or in use conditions, e.g. under baby weight.

Fastening System

The absorbent article may include a fastening system. The fastening system can be used to provide lateral tensions about the circumference of the absorbent article to hold the absorbent article on the wearer. This fastening system is not necessary for training pant article since the waist region of these articles is already bonded. The fastening system usually comprises a fastener 42 such as tape tabs, hook and loop fastening components, interlocking fasteners such as tabs & slots, buckles, buttons, snaps, and/or hermaphroditic fastening components, although any other known fastening means are generally acceptable. A landing zone is normally provided on the front waist region of the article for the fastener 42 to be releasably attached. Some exemplary surface fastening systems are disclosed in U.S. Pat. Nos. 3,848,594, 4,662,875, 4,846,815, 4,894,060, 4,946,527, 5,151,092 and 5,221,274 (Buell). An exemplary interlocking fastening system is disclosed in U.S. Pat. No. 6,432,098. The fastening system may also provide a means for holding the article in a disposal configuration as disclosed in U.S. Pat. No. 4,963,140 (Robertson et al.)

The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499,978, 5,507,736, and 5,591,152.

Front and Back Ears 46, 40

The absorbent article may comprise front ears 46 and back ears 40 as is known in the art. The ears can be integral part of the chassis, for example formed from the topsheet and/or backsheet as side panel. Alternatively, as represented in FIG. 2, they may be separate elements attached by gluing and/or heat embossing. The back ears 40 are advantageously stretchable to facilitate the attachment of the tabs 42 on the landing zone 44 and maintain the taped diapers in place around the wearer's waist. The front ears 46 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Barrier Leg Cuffs 34 and Gasketing Cuffs 32

Absorbent articles such as diapers or training pants may typically further comprise components that improve the fit of the article around the legs of the wearer, in particular barrier leg cuffs 34 and gasketing cuffs 32. The barrier leg cuffs 32 may be formed by a piece of material, typically a nonwoven, which is partially bonded to the rest of the article and can be partially raised away and thus stand up from the plane defined by the topsheet, when the article is pulled flat as shown for example in FIG. 3. The barrier leg cuffs 34 can provide improved containment of liquids and other body exudates approximately at the junction of the torso and legs of the wearer. The barrier leg cuffs 34 extend at least partially between the front edge and the back edge of the absorbent article on opposite sides of the longitudinal axis and are at least present adjacent to the crotch point (C) of the core.

The barrier leg cuffs 34 may be delimited by a proximal edge 64 joined to the rest of the article, typically the topsheet and/or the backsheet, and a free terminal edge 66 intended to contact and form a seal with the wearer's skin. The barrier leg cuffs 34 may be joined at the proximal edge 64 with the chassis of the article by a bond 65 which may be made for example by adhesive bonding, fusion bonding or combination of known bonding means. The bond 65 at the proximal edge 64 may be continuous or intermittent.

The barrier leg cuffs 34 can be integral with (i.e. formed from) the topsheet or the backsheet, or more typically be formed from a separate material joined to the rest of the article. Typically the material of the barrier leg cuffs may extend through the whole length of the article but is "tack bonded" to the topsheet towards the front edge and back edge of the article so that in these sections the barrier leg cuff material remains flush with the topsheet. Each barrier leg cuff 34 may comprise one, two or more elastic strings 35 close to this free terminal edge 66 to provide a better seal.

In addition to the barrier leg cuffs 34, the article may comprise gasketing cuffs 32, which are formed in the same plane as the chassis of absorbent article, in particular may be at least partially enclosed between the topsheet and the backsheet, and may be placed laterally outwardly relative to the barrier leg cuffs 34. The gasketing cuffs 32 can provide a better seal around the thighs of the wearer. Usually each gasketing leg cuff 32 will comprise one or more elastic string or elastic element 33 comprised in the chassis of the diaper for example between the topsheet and backsheet in the area of the leg openings.

U.S. Pat. No. 3,860,003 describes a disposable diaper which provides a contractible leg opening having a side flap and one or more elastic members to provide an elasticized leg cuff (a gasketing cuff). U.S. Pat. No. 4,808,178 (Aziz) and U.S. Pat. No. 4,909,803 (Aziz) describe disposable diapers having "stand-up" elasticized flaps (barrier leg cuffs) which improve the containment of the leg regions. U.S. Pat. No. 4,695,278 (Lawson) and U.S. Pat. No. 4,795,454 (Dragoo) describe disposable diapers having dual cuffs, including gasketing cuffs and barrier leg cuffs. All or a portion of the barrier leg and/or gasketing cuffs may be treated with a lotion.

Elastic Waist Feature

The absorbent article may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core 28 and generally forms at least a portion of the back side of the absorbent article. Disposable diapers can be constructed so as to have two elastic waist features, one positioned in the front waist region and one positioned in the back waist region. The elastic waist feature may be constructed in a number of different configurations including those described in U.S. Pat. Nos. 4,515,595, 4,710,189, 5,151,092 and 5,221,274.

Relations Between the Layers and Components

Apart from the core-to-backsheet gluing pattern described in details previously, adjacent layers may be joined together using conventional bonding method such as adhesive coating via slot coating or spraying on the whole or part of the surface of the layer, or thermo-bonding, or pressure bonding or combinations thereof. Most of the bonding between components is for clarity and readability not represented in the Figure. Bonding between the layers of the article should be considered to be present unless specifically excluded. Adhesives may be typically used to improve the adhesion of the different layers, for example between the backsheet and the core wrap. The adhesives used may be any standard hotmelt glue as known in the art.

Method of Making

Apart from the method for applying the gluing pattern described in details previously, the absorbent article may be made otherwise by any conventional methods known in the art. In particular the articles may be hand-made or industrially produced at high speed on a modern converting line.

Test Procedures

The values indicated herein are measured according to the methods indicated herein below, unless specified otherwise. All measurements are performed at 21° C.±2° C. and 50%±20% RH, unless specified otherwise. All samples should be kept at least 24 hours in these conditions to equilibrate before conducting the tests, unless indicated otherwise. All measurements should be reproduced on at least 4 samples and the average value obtained indicated, unless otherwise indicated.

Centrifuge Retention Capacity (CRC)

The CRC measures the liquid absorbed by the superabsorbent polymer particles for free swelling in excess liquid. The CRC is measured according to EDANA method WSP 241.2-05.

Dry Absorbent Core Caliper Test

This test may be used to measure the caliper of the absorbent core (before use i.e. without fluid loading) in a standardized manner.

Equipment: Mitutoyo manual caliper gauge with a resolution of 0.01 mm, or equivalent instrument.

Contact Foot: Flat circular foot with a diameter of 17.0 mm (±0.2 mm). A circular weight may be applied to the foot (e.g., a weight with a slot to facilitate application around the instrument shaft) to achieve the target weight. The total weight of foot and added weight (including shaft) is selected to provide 2.07 kPa (0.30 psi) of pressure to the sample.

The caliper gauge is mounted with the lower surface of the contact foot in an horizontal plane so that the lower surface of the contact foot contacts the center of the flat horizontal upper surface of a base plate approximately 20×25 cm. The gauge is set to read zero with the contact foot resting on the base plate.

Ruler: Calibrated metal ruler graduated in mm.

Stopwatch: Accuracy 1 second.

Sample preparation: The core is conditioned at least 24 hours as indicated above.

Measurement procedure: The core is laid flat with the bottom side, i.e. the side intended to be placed towards the backsheet in the finished article facing down. The point of measurement (e.g. the crotch point C) is carefully drawn on the top side of the core taking care not to compress or deform the core.

The contact foot of the caliper gauge is raised and the core is placed flat on the base plate of the caliper gauge with the top side of the core up so that when lowered, the center of the foot is on the marked measuring point.

The foot is gently lowered onto the article and released (ensure calibration to "0" prior to the start of the measurement). The caliper value is read to the nearest 0.01 mm, 10 seconds after the foot is released.

The procedure is repeated for each measuring point. If there is a fold at the measuring point, the measurement is done in the closest area to this point but without any folds. Ten articles are measured in this manner for a given product and the average caliper is calculated and reported with an accuracy of one tenth mm.

Absorbent Article Caliper Test

The Absorbent Article Caliper Test can be performed as for the Dry Absorbent Core Caliper Test with the difference that the caliper of the finished absorbent article is measured instead of the caliper of the core. The point of measurement may correspond vertically with the crotch point of the core as defined earlier. If the absorbent articles were provided folded and/or in a package, the articles to be measured are unfolded and/or removed from the center area of the package. If the package contains more than 4 articles, the outer most two articles on each side of the package are not used in the testing. If the package contains more than 4 but fewer than 14 articles, then more than one package of articles is required to complete the testing. If the package contains 14 or more articles, then only one package of articles is required to perform the testing. If the package contains 4 or fewer articles then all articles in the package are measured and multiple packages are required to perform the measurement. Caliper readings should be taken 24±1 hours after the article is removed from the package, unfolded and conditioned. Physical manipulation of product should be minimal and restricted only to necessary sample preparation.

Any elastic components of the article that prevent the article from being laid flat under the caliper foot are cut or removed. These may include leg cuffs or waistbands. Pant-type articles are opened or cut along the side seams as necessary. Apply sufficient tension to flatten out any folds/wrinkles Care is taken to avoid touching and/or compressing the area of measurement.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for personal hygiene having a wearer-facing side, a garment-facing side and a longitudinal axis, the article comprising:
    a topsheet on the wearer-facing side;
    a backsheet on the garment-facing side;
    an absorbent core between the topsheet and the backsheet, the absorbent core comprising:
        an absorbent material comprising a superabsorbent polymer;
        a core wrap enclosing the absorbent material;
        a first channel disposed on one side of the longitudinal axis and a second channel disposed on the other side of the longitudinal axis, and an area between the channels;
    wherein the absorbent core is attached to the backsheet at least by:
        a first glue, having a first glue application area and a first glue application pattern, wherein the first glue application area is at least partially disposed in the area between the channels; and
        a second glue, having a second glue application area and a second glue application pattern, wherein the second glue application area is at least partially outside the area between the channels, and
            wherein the first channel and second channel are at least partially not attached by the first glue and second glue to the backsheet, and
            wherein the first glue application pattern differs from the second glue application pattern.

2. The absorbent article according to claim 1 wherein the first glue application pattern is continuous.

3. The absorbent article according to claim 2, wherein the first glue is slot-coated.

4. The absorbent article according to claim 1, wherein the second glue application pattern is discontinuous.

5. The absorbent article according to claim 4, wherein the second glue application pattern is at least one of a plurality of large swirls, a plurality of mini-swirls or randomly deposited adhesive fibers.

6. The absorbent article according to claim 1, wherein the second glue application area is larger than the first glue application area.

7. The absorbent article according to claim 6, wherein the second glue application area is at least 3 times larger than the first glue application area.

8. The absorbent article according to claim 1, wherein the second glue application area comprises at least a first portion on one side of longitudinal axis and at least a second portion on the other side of the longitudinal axis, and both portions extend along the full length of the absorbent core.

9. The absorbent article according to claim 8, wherein the first and second portion of the second glue application area extend along the full length of the backsheet.

10. The absorbent article according to claim 8, wherein the absorbent core has a first and a second longitudinally extending side edges, and the longitudinally extending first portion is at least partially present between the first longitudinally extending side edge and the first channel, and the longitudinally extending second portion is at least partially present between the second longitudinally extending side edge of the core and the second channel.

11. The absorbent article according to claim 1, wherein the absorbent core has a front edge and a back edge, and said front and back edges are attached along their entire widths by a front portion and a back portion of the second glue application area respectively.

12. The absorbent article according to claim 1, wherein the second glue application area approximately has a roman II numeral shape.

13. The absorbent article according to claim 1, wherein the absorbent material of the absorbent core comprises less than 20% of cellulosic fibers, by weight of the absorbent material.

14. The absorbent article according to claim 13, wherein the absorbent material is free of cellulosic fibers.

15. The absorbent article according to claim 1 wherein the channels are areas substantially free of absorbent material which are surrounded by absorbent material.

16. The absorbent article according to claim 1, wherein a top side and a bottom side of the core wrap are attached to each other through the channels.

17. The absorbent article according to claim 1, wherein the first channel and the second channel are longitudinally extending and each have a length as projected on the longitudinal axis which is at least 25% of the length of the absorbent core.

* * * * *